US011775879B2

(12) United States Patent
 Watanabe

(10) Patent No.: US 11,775,879 B2
(45) Date of Patent: Oct. 3, 2023

(54) APPARATUS, ROOM, MANAGEMENT SYSTEM, AND NON-TRANSITORY COMPUTER READABLE MEDIUM

(71) Applicant: FUJIFILM Business Innovation Corp., Tokyo (JP)

(72) Inventor: Shu Watanabe, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 1159 days.

(21) Appl. No.: 16/109,781

(22) Filed: Aug. 23, 2018

(65) Prior Publication Data

US 2019/0130317 A1    May 2, 2019

(30) Foreign Application Priority Data

Oct. 26, 2017    (JP) ................................. 2017-207331

(51) Int. Cl.
 *G06Q 10/02*    (2012.01)
 *G01N 33/00*    (2006.01)

(52) U.S. Cl.
 CPC .......... *G06Q 10/02* (2013.01); *G01N 33/0004* (2013.01)

(58) Field of Classification Search
 CPC ..... G06Q 10/02; G01N 33/004; G01N 1/2273
 USPC ........................................................... 705/5
 See application file for complete search history.

(56) References Cited

U.S. PATENT DOCUMENTS

| 9,810,446 B2 | 11/2017 | Harada et al. |
| 2009/0053989 A1* | 2/2009 | Lunde .................. G01N 1/2273 29/700 |
| 2017/0161646 A1* | 6/2017 | Abuelsaad .............. G06F 16/29 |
| 2018/0204162 A1* | 7/2018 | Endel ............... G06Q 10/06315 |

FOREIGN PATENT DOCUMENTS

| CN | 106500253 A | * | 3/2017 | |
| JP | 2004-086582 | | 3/2004 | |
| JP | 2016027293 | | 2/2016 | |
| JP | 2016027293 A | * | 2/2016 | ......... F24D 19/1084 |
| JP | 2017091293 | | 5/2017 | |
| JP | 2017091293 A | * | 5/2017 | |
| JP | 2022078420 A | * | 5/2022 | |
| WO | WO-2012160467 A1 | * | 11/2012 | ............. G06Q 10/06 |

OTHER PUBLICATIONS

Roxburgh, Helen, "How clean indoor air is becoming China's latest luxury must-have", Mar. 27, 2018, the guardian.com; 11 pages (Year: 2018).*
Office Action of Japan Counterpart Application, with English translation thereof, dated Jun. 29, 2021, pp. 1-6.

* cited by examiner

*Primary Examiner* — Shannon S Campbell
*Assistant Examiner* — Freda A Nelson
(74) *Attorney, Agent, or Firm* — JCIPRNET

(57) ABSTRACT

An apparatus includes an estimator. The estimator estimates, based on a reservation status, an air quality within a space at a start time of a reservation to be made for the space.

27 Claims, 24 Drawing Sheets

FIG. 15A

STEP 1

| | 6 7 8 9 10 11 12 1 2 3 4 5 6 7 8 9 10 11 |
|---|---|
| #001 | |
| #002 | |
| #003 | |
| #004 | |

East Exist of Station Y on Line C

FIG. 15B

STEP 2

| | 6 7 8 9 10 11 12 1 2 3 4 5 6 7 8 9 10 11 |
|---|---|
| #001 | |
| #002 | |
| #003 | |
| #004 | |

East Exist of Station Y on Line C

250

FIG. 15C
STEP 3

| | 6 | 7 | 8 | 9 | 10 | 11 | 12 | 1 | 2 | 3 | 4 | 5 | 6 | 7 | 8 | 9 | 10 | 11 |
|---|---|---|---|---|---|---|---|---|---|---|---|---|---|---|---|---|---|---|
| #001 | | | | | | | | | | | | | | | | | | |
| #002 East Exist of Station Y on Line C | | | | | | | | | | | | | | | | | | |
| #003 | | | | | | | | | | | | | | | | | | |
| #004 | | | | | | | | | | | | | | | | | | |

251

FIG. 15D
STEP 4

| | 6 | 7 | 8 | 9 | 10 | 11 | 12 | 1 | 2 | 3 | 4 | 5 | 6 | 7 | 8 | 9 | 10 | 11 |
|---|---|---|---|---|---|---|---|---|---|---|---|---|---|---|---|---|---|---|
| #001 East Exist of Station Y on Line C | | | | | | | | | | | | | | | | | | |
| #002 | | | | | | | | | | | | | | | | | | |
| #003 | | | | | | | | | | | | | | | | | | |
| #004 | | | | | | | | | | | | | | | | | | |
| #001 South Exit of Station X on Line B | | | | | | | | | | | | | | | | | | |
| #002 | | | | | | | | | | | | | | | | | | |
| #003 | | | | | | | | | | | | | | | | | | |
| #004 | | | | | | | | | | | | | | | | | | |

| | IN PREPARATION → | READY → | BEING USED |
|---|---|---|---|
| OUTDOOR LED | BLINK | ON | OFF |
| INDOOR LIGHTING | OFF OR GLIMMER | OFF OR GLIMMER | ON |
| UV LED | ON | OFF | OFF |
| AIR CONDITIONER | URGENT MODE OR REGULAR MODE | OFF | REGULAR MODE OR OFF |
| VENTILATION VENT UNIT | FULL OPEN | FULL OPEN OR HALF OPEN | HALF OPEN BUT AUTOMATICALLY CLOSED DURING USE (FULL OPEN BY USER OPERATION) |

APPARATUS, ROOM, MANAGEMENT SYSTEM, AND NON-TRANSITORY COMPUTER READABLE MEDIUM

CROSS-REFERENCE TO RELATED APPLICATIONS

This application is based on and claims priority under 35 USC 119 from Japanese Patent Application No. 2017-207331 filed Oct. 26, 2017.

BACKGROUND

(i) Technical Field

The present invention relates to an apparatus, a room, a management system, and a non-transitory computer readable medium.

(ii) Related Art

Services for providing the use of a space to a reservation holder are available.

SUMMARY

According to an aspect of the invention, there is provided an apparatus including an estimator. The estimator estimates, based on a reservation status, an air quality within a space at a start time of a reservation to be made for the space.

BRIEF DESCRIPTION OF THE DRAWINGS

Exemplary embodiments of the present invention will be described in detail based on the following figures, wherein:

FIGS. 15A through 15D illustrate examples of a reservation process conducted under the control operation;

FIG. 20 illustrates examples of the states of equipment installed in a space at individual time points when the space is in preparation, ready, and being used;

DETAILED DESCRIPTION

Exemplary embodiments of the invention will be described below with reference to the accompanying drawings.

Exemplary Embodiment

[Overall Configuration of Management System]

Due to the increased communication speed and smaller communication terminals, users can now access various items of information even outside the office. On the other hand, however, business conversations and information are highly confidential, and quiet and high-security environments are desirably provided.

In this exemplary embodiment, a management system for providing spaces that satisfy such a demand will be described. Spaces, which will be described below, are not restricted for business use, but may also be for personal use.

Figure 1:
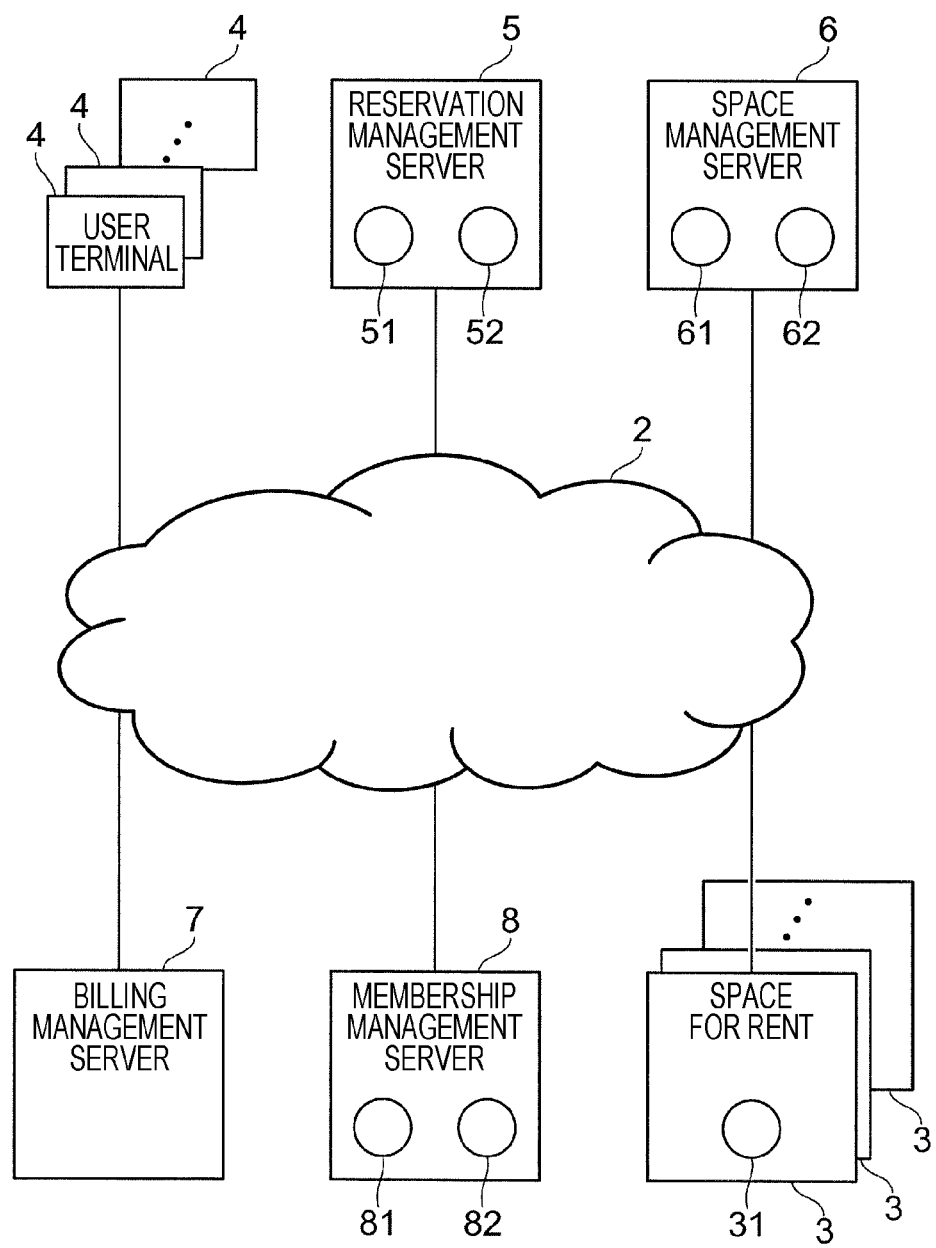
FIG. 1 schematically illustrates an example of the overall configuration of a management system.

FIG. 1 schematically illustrates an example of the overall configuration of a management system 1.

As shown in FIG. 1, the management system 1 is constituted by various terminals connected to a cloud network 2.

In the example in FIG. 1, the management system 1 includes multiple spaces 3 for rent, multiple user terminals 4, a reservation management server 5, a space management server 6, a billing management server 7, and a membership management server 8. The spaces 3 for rent are spaces to be rented on a time basis. Hereinafter, the spaces 3 for rent may simply be called the spaces 3. The user terminals 4 are carried by individual users using the spaces 3. The reservation management server 5 manages reservations for the spaces 3. The space management server 6 manages the usage statuses of the individual spaces 3. The billing management server 7 bills users for the use of the spaces 3. The membership management server 8 manages information concerning members entitled to use the spaces 3.

The spaces 3 are available twenty-four hours a day, seven days a week (24/7), except for the time reserved for maintenance, for example.

In the management system 1 shown in FIG. 1, one server is provided for one purpose (function). Alternatively, plural servers may be provided for one purpose (function). Conversely, one server may be provided for multiple purposes (functions).

Renting services for the spaces 3 may be provided by one business operator or plural business operators. For example, different business operators may separately conduct management concerning reservations, access to and usage statuses of the spaces 3, billing for the use of the spaces 3, and members registered as users. Alternatively, multiple business operators may conduct management concerning one purpose (function) collaboratively.

Plural servers may be provided for one purpose (function). If a single business operator provides plural servers for one purpose (function) or provides plural servers for multiple purposes (functions), the plural servers are connected to each other via an intranet.

The spaces 3 may be provided by a single business operator or plural business operators.

The management system 1 may be implemented as an aggregation of services provided by plural business operators.

In this exemplary embodiment, a digital key is used for locking and unlocking a space 3. A digital key is stored in a user terminal 4 or an integrated circuit (IC) card which supports near field communication (NFC) (not shown). If a user terminal 4 is used as a digital key, a digital key is provided from the reservation management server 5 to the user terminal 4 after a reservation is confirmed. If an IC card is used as a digital key, an IC card having a digital key recorded thereon is distributed from the reservation management server 5 to a user terminal 4 after a reservation is confirmed.

The use of a digital key makes it possible to freely determine an effective time period for which a space 3 can be locked and unlocked. Multiple digital keys for using one space 3 for the same time period may be issued.

Alternatively, multiple physical keys may be provided according to the reserved time to lock and unlock a space 3. User authentication may alternatively be conducted instead of the use of a key or as a function for supporting the use of a digital key or a physical key.

The reservation management server 5 manages a registration list 51 and a reservation list 52. In the registration list 51, vacancies for spaces 3 are registered. The reservation management server 5 manages the allocation of reservation holders to the spaces 3 by using the reservation list 52.

In this exemplary embodiment, the reservation management server 5 receives reservation requests for the spaces 3 24/7, except for the time reserved for maintenance, for example. The reservation management server 5 also issues digital keys to the user terminals 4 and conducts authentication if necessary. The space management server 6 may alternatively conduct authentication.

The space management server 6 manages information 61 concerning access to the individual spaces 3 and information 62 concerning the usage statuses of the individual spaces 3. The space management server 6 also serves the function of communicating with an authentication unit 32A (see FIG. 2) disposed in a space 3 to decide whether to permit a user to enter this space 3. When conducting authentication, the space management server 6 communicates with the reservation management server 5.

The space management server 6 also serves the function of collecting information from various devices 31 disposed in a space 3 and controlling the various devices 31.

The space management server 6 is connected to the cloud network 2 in FIG. 1. However, some or all of the functions of the space management server 6 may be integrated in a space 3.

The billing management server 7 serves the function of billing an individual member (may be a natural person (individual) or a legal person (enterprise)) based on reservation information, user information, information concerning access to a space 3. The billing management server 7 obtains reservation information from the reservation management server 5, information concerning access to a space 3 from the space management server 6, and membership information from the membership management server 8.

The membership management server 8 manages information concerning registered members and information concerning users. If a member is an individual person, the member is a user using a space 3. If a member is an enterprise, individual users are registered and managed according to the member.

Figure 2:
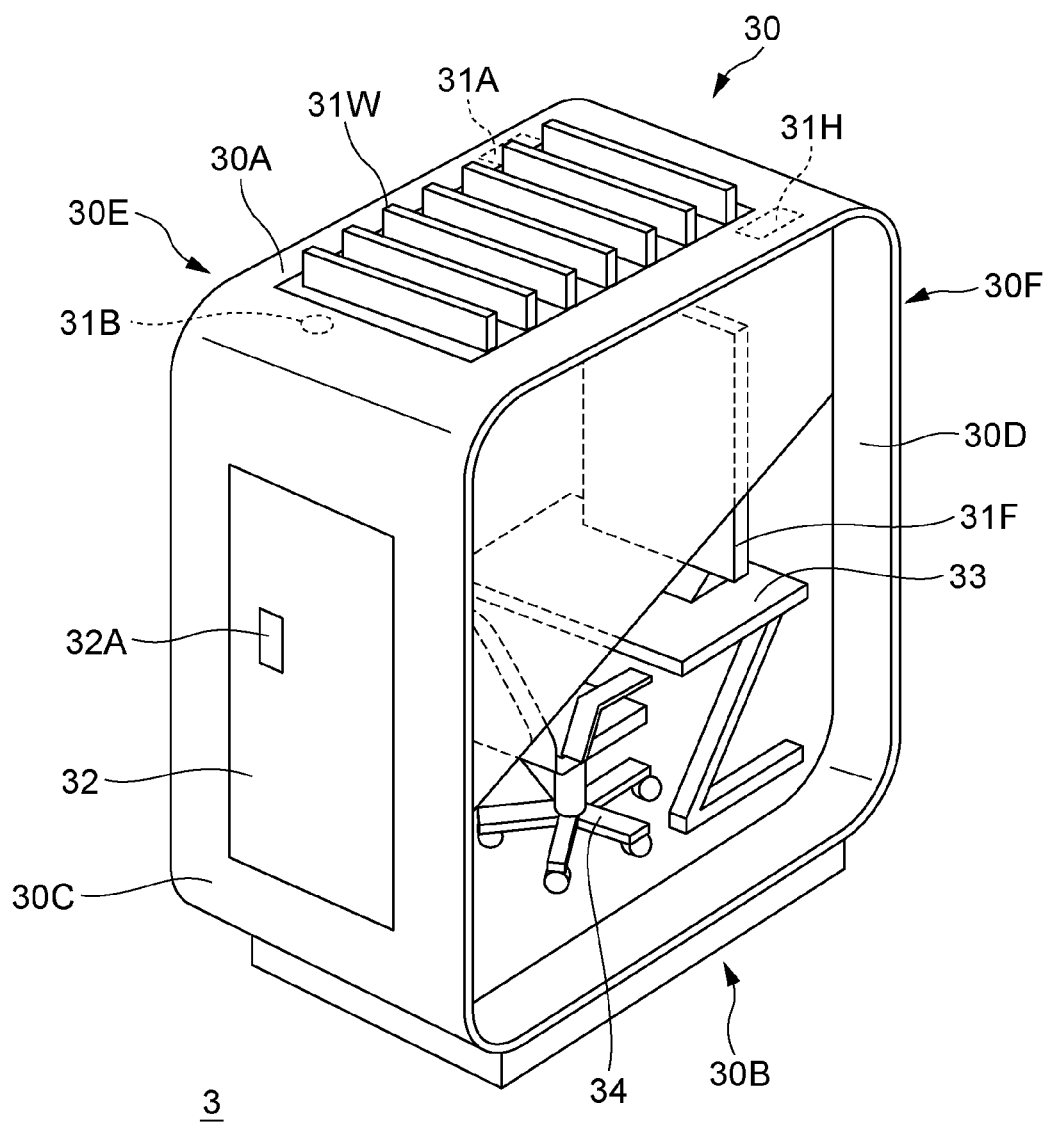
FIG. 2 is an external view of an example of the configuration of a space to be rented to a user.

FIG. 2 is an external view of an example of the configuration of a space 3 to be rented to a user.

In this exemplary embodiment, the spaces 3 are disposed indoors and outdoors, such as in station buildings, airports, office buildings, commercial complexes, for example, restaurants and department stores, banks, libraries, art galleries, museums, public institutions and facilities, passageways, and parks.

In this exemplary embodiment, a soundproof, small room is assumed as a space 3. In this sense, the space 3 is an example of a closed space. In this exemplary embodiment, however, "closed" does not mean "sealed", but is used in the sense of a space having a practical soundproof function. Openings and gaps, such as vent holes and small windows, may be provided in part of a skeleton 30 forming a space 3.

The skeleton 30 includes a ceiling 30A, a floor 30B, a wall 30C to which a door 32 is fixed, two walls 30D and 30E at both sides of the wall 30C, and a wall 30F opposite the door 32.

In this exemplary embodiment, a single hinged door is assumed as the door 32. In the single hinged door, a single door member is opened and closed such that it draws an arc. However, the door 32 may be a double hinged door having two door members.

The door 32 may be a sliding door. The sliding door may be a single sliding door in which one door member slides, a multiple sliding door set in which two or more door members slide in opposite directions on different rails, or a separate double sliding door set in which one door member slides to the left and the other door member slides to the right.

The door 32 may be a folding door in which a pair of door members connected by a hinge opens to fold back. The folding door has a single type which opens to one side and a double type which opens to two sides.

The door 32 may be a special door, such as a partition door or a pocket door which is withdrawn into a wall when it is not used.

The door 32 may be an inward opening type or an outward opening type.

In this exemplary embodiment, the walls 30D and 30E are partly constituted by a light-transmitting member, such as glass and acrylic resin, for example.

The structure, material, or processing to implement a blind function may be utilized for at least part of the walls 30D and 30E. The blind function makes it difficult to see the inside of the space 3 from the outside or to reduce the visibility through the walls 30D and 30E.

The material of the walls 30D and 30E may be a translucent member or a member with small scratches on its surface so as to cause light to scatter. A film-like member having a similar function may be attached to the walls 30D and 30E. The film-like member may be a liquid crystal film that can electrically switch between a transparent state and an opaque state or a polarizing film that can electrically control the luminous transmittance.

A structure or a member for a blind function may be provided separately. The walls 30D and 30E, as well as the other surfaces, may be made of a member that does not transmit light. Conversely, among the elements forming the skeleton 30, three or more surfaces may be made of a transparent or translucent member.

The number of users using a space 3 is largely determined by the volume of this space 3. Basically, in this exemplary embodiment, a private room for one person is assumed as a space 3. However, the space 3 may be a large room for accommodating a large group of people. A large room may be formed as one room, or it may be formed by interconnecting spaces 3 by removing one of or both of the walls 30D and 30E of each space 3.

A private room is not necessarily for only one person, and may be used for a few people, such as two or three people.

The configuration and structure of the skeleton 30 forming an individual space 3, and facilities to be provided by the space 3 and their performance may be determined as desired.

In this exemplary embodiment, one desk 33 and one chair 34 are disposed within the skeleton 30. On the desk 33, a display device 31F, which is an example of devices 31, is placed. If a fixed computer (not shown) is provided, data and history information stored in the computer are all deleted under the control of the system after the use of the space 3 to protect user information.

As the other devices 31, an air conditioner 31A, a ventilation vent unit 31W, a human sensor 31B, a control device 31H, and an authentication unit 32A are fixed. The control device 31H controls the operation of electronic devices including the devices 31.

The devices 31 are only examples of electronic devices. Although in FIG. 2 the display device 31F is placed on the desk 33, it may not be necessarily provided. In this case, a user uses its own computer or smartphone.

The entirety of the space 3 (including the skeleton 30) is an example of an apparatus and is also an example of a room. Each of the user terminal 4, the reservation management server 5, the space management server 6, the billing management server 7, and the membership management server 8 is also an example of the apparatus.

The management system 1 is an example of a management system.

[Configuration of Terminal]

Examples of the configurations of the terminals forming the management system 1 will be discussed below with reference to FIGS. 3 through 5.

Figure 3:
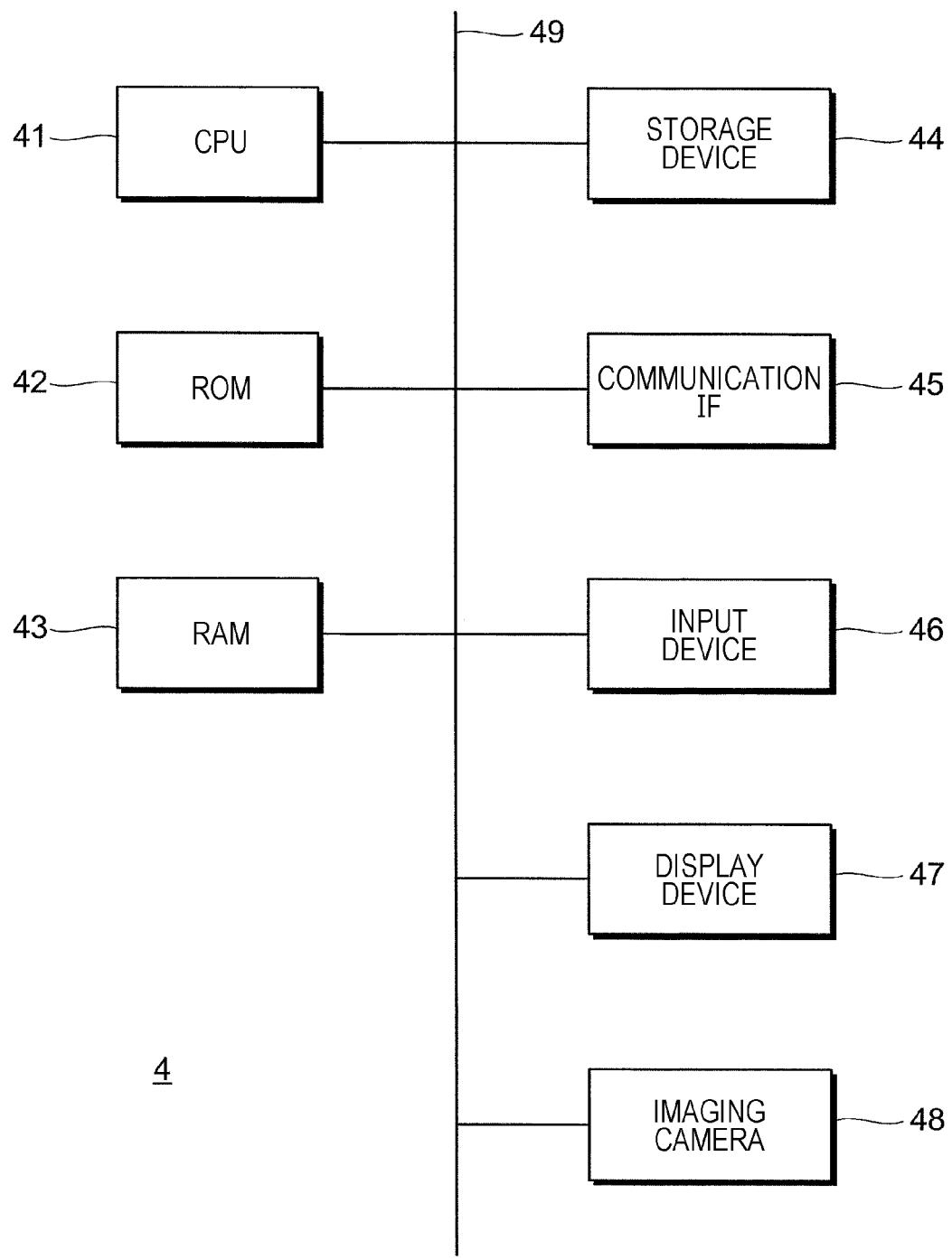
FIG. 3 is a block diagram illustrating an example of the hardware configuration of a user terminal.

FIG. 3 is a block diagram illustrating an example of the hardware configuration of the user terminal 4.

In this exemplary embodiment, a smartphone is used as the user terminal 4.

The user terminal 4 includes a central processing unit (CPU) 41, a read only memory (ROM) 42, and a random access memory (RAM) 43. The CPU 41 provides various functions by executing firmware and application programs. The ROM 42 is a storage area in which firmware and basic input output system (BIOS) are stored. The RAM 43 is an area where a program is executed.

The user terminal 4 also includes a volatile storage device 44, a communication interface 45 (communication IF), an input device 46, such as a touchscreen, a display device 47, and an imaging camera 48. The storage device 44, which is a semiconductor memory, for example, stores downloaded application programs and a digital key, for example. The communication IF 45 is used for communicating with external devices. The display device 47 is used for displaying information.

The CPU 41 is connected to the devices forming the user terminal 4 via a bus 49.

Figure 4:
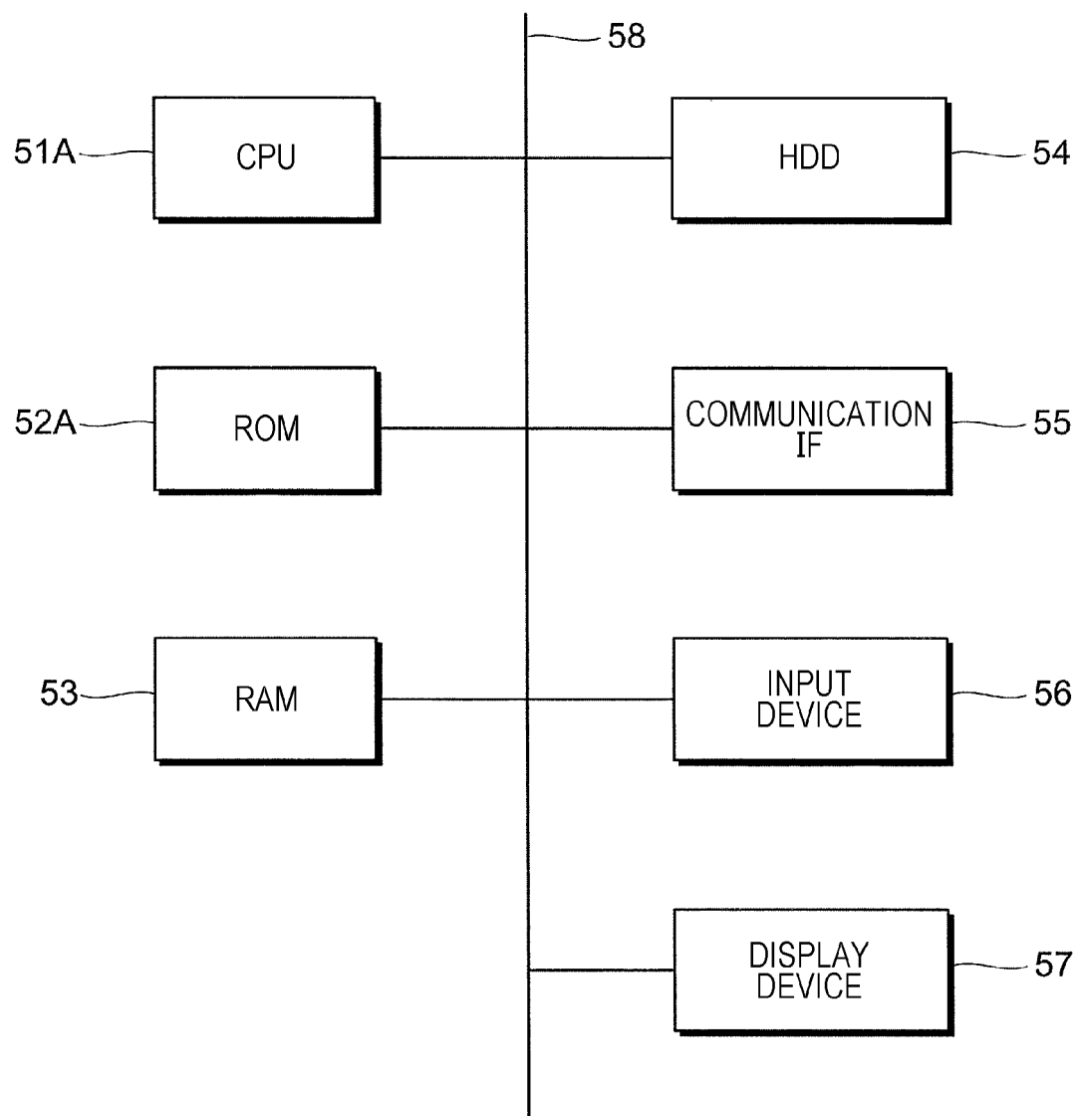
FIG. 4 is a block diagram illustrating an example of the hardware configuration of a server forming the management system.

FIG. 4 is a block diagram illustrating an example of the hardware configuration of a server forming the management system 1.

The configuration of the reservation management server 5 is shown in FIG. 4 as a typical example of the server. The configurations of the other servers, that is, the space management server 6, the billing management server 7, and the membership management server 8, are similar to the configuration of the reservation management server 5.

The reservation management server 5 includes a CPU 51A, a ROM 52A, and a RAM 53. The CPU 51A provides various management functions by executing an operating system (OS) and application programs. The ROM 52A is a storage area in which an OS and a BIOS are stored. The RAM 53 is an area where a program is executed.

The reservation management server 5 also includes a volatile hard disk drive (HDD) 54, a communication IF 55, an input device 56, such as a keyboard, and a display device 57. The HDD 54 stores application programs and various items of management data for implementing the associated management functions. The communication IF 55 is used for communicating with external devices. The display device 57 is used for displaying information.

The CPU 51A is connected to the devices via a bus 58.

Each server is an example of a database for storing management data.

Figure 5:
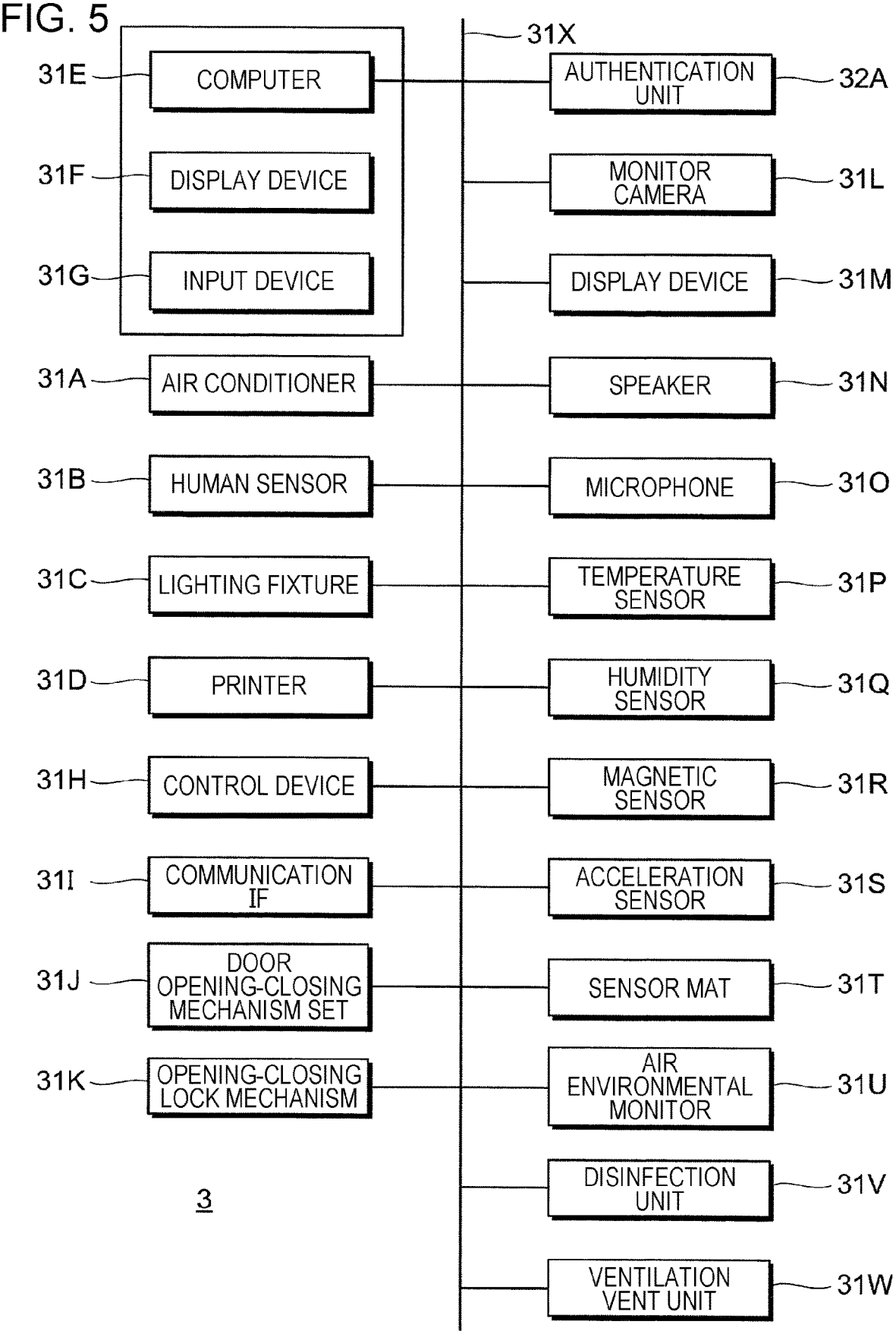
FIG. 5 is a block diagram illustrating an example of the configuration of a space which forms the management system.

FIG. 5 is a block diagram illustrating an example of the configuration of a space 3 which forms the management system 1.

The space 3 includes an air conditioner 31A, a human sensor 31B, a lighting fixture 31C, a printer 31D, a computer 31E, a display device 31F, an input device 31G, a control device 31H, and an authentication unit 32A.

The air conditioner 31A is used for adjusting the temperature and humidity within the space 3 (room). A mechanism specially used for ventilation (ventilation device) may be provided, together with or separately from the air conditioner 31A. The ventilation device includes an air supply unit which supplies fresh air into a room and an exhaust unit which exhausts air in the room outside. The ventilation vent unit 31W, which will be discussed later, is part of the ventilation device.

The human sensor 31B is a sensor for detecting people within the space 3. As the human sensor 31B, various types of sensors, such as a pyroelectric infrared human sensor that can detect the motion of people, and an image human sensor and a thermopile human sensor that can detect the number and position of people, are available. One or plural of these types of sensors are used according to the purpose of use.

The printer 31D, the computer 31E, the display device 31F, and the input device 31G are examples of information devices installed in the room for a user to operate. These information devices are connected to each other via a local area network (LAN) 31X, such as a LAN cable or a wireless LAN. If a user brings its own computer, the computer is connected to the LAN 31X. As the wireless LAN, WiFi (registered trademark) or Bluetooth (registered trademark) is used.

The control device 31H is a control computer that collects information from the devices 31 connected to the LAN 31X and also controls the operations of the individual devices 31.

In some management systems 1, the control device 31H provides the functions of the space management server 6.

The authentication unit 32A is fixed to the door 32 of the space 3, for example. The authentication unit 32A is used for obtaining and sending and receiving information required for locking and unlocking the door 32. Authentication is conducted in the reservation management server 5, and an authentication result is only supplied to the authentication unit 32A. When authentication has succeeded, the authentication unit 32A unlocks the door 32. After unlocking the door 32, a user can open and close the door 32 to enter the space 3 (see FIG. 2).

The space 3 also includes a communication IF 311 for communicating with external devices. The communication IF 311 is connected to the cloud network 2 (see FIG. 1) to communicate with various servers.

The space 3 also includes a door opening-closing mechanism set 31J for mechanically controlling the opening and closing of the door 32. The door opening-closing mechanism set 31J includes a mechanism for driving the door 32 to open and close and a mechanism for adjusting the magnitude of a load required for a user to open and close the door 32.

The space 3 also includes an opening-closing lock mechanism 31K. The opening-closing lock mechanism 31K temporarily stops the opening and closing of the door 32. While the opening-closing lock mechanism 31K is in operation, at least the operation of closing the door 32 is temporarily stopped.

The space 3 also includes a monitor camera 31L for monitoring the motion of users indoors and outdoors. However, the monitor camera 31L may not necessarily be provided.

The space 3 also includes a display device 31M. In this exemplary embodiment, the display device 31M is disposed on the external side of the wall 30C to which the door 32 is fixed, and is used for a user to operate when entering the space 3 and also for providing information. The display device 31M is also used for a user using the space 3 and also for providing information. The display device 31M is an example of an informing device.

The space 3 also includes a speaker 31N. The speaker 31N is used for supplying information to a user indoors and to people outdoors. The speaker 31N is an example of the informing device.

The space 3 also includes a microphone 31O. The microphone 31O is used for collecting indoor sound.

The space 3 also includes a temperature sensor 31P. The temperature sensor 31P is used for measuring the indoor temperature.

The space 3 also includes a humidity sensor 31Q. The humidity sensor 31Q is used for measuring the indoor humidity.

The space 3 also includes a magnetic sensor 31R. The magnetic sensor 31R is attached to the door 32 to detect the opening or closing of the door 32 by sensing a magnetic force.

The space 3 also includes an acceleration sensor 31S. The acceleration sensor 31S is used for detecting the motion of an object.

The space 3 also includes a sensor mat 31T. The sensor mat 31T detects the weight of an object to visualize the time period for which a user has stayed in the space 3 or the congestion status of the space 3.

The space 3 also includes an air environmental monitor 31U. The air environmental monitor 31U, which detects constituents contained in air in the space 3, measures concentrations of PM2.5 and PM10, carbon dioxide, and volatile organic compounds. The air environmental monitor 31U may also measure the temperature and the humidity. The air environmental monitor 31U may not necessarily measure all of the above-described constituents or may measure other constituents. If the air environmental monitor 31U measures the temperature and the humidity, the provision of the temperature sensor 31P and the humidity sensor 31Q may be omitted.

A disinfection unit 31V is provided for disinfecting a room. In this exemplary embodiment, a light source for emitting ultraviolet (UV) rays (hereinafter called the UV light source) and a deodorizing spray is used.

As the UV light source, a UV light emitting diode (LED) is used. In this exemplary embodiment, the UV light source is turned ON when nobody is in a room and is turned OFF when somebody is in a room.

In this exemplary embodiment, both of the UV light source and the deodorizing spray are disposed as the disinfection unit 31V. However, only one of them may be disposed.

The ventilation vent unit 31W is attached to the ceiling 30A (see FIG. 2) for ventilation. The ventilation vent unit 31W is closed when someone is in a room and forms part of the ceiling 30A, and is opened when ventilating the room. The ventilation vent unit 31W forms part of the ventilation device, which is not shown.

[Control Function]

A control function implemented by one of the terminals forming the management system 1 or by collaborative work of some of the terminals will be discussed below with reference to FIG. 6.

A description will be given of a case in which the control function is implemented by the CPU 51A (see FIG. 4) of the reservation management server 5 alone.

Figure 6:
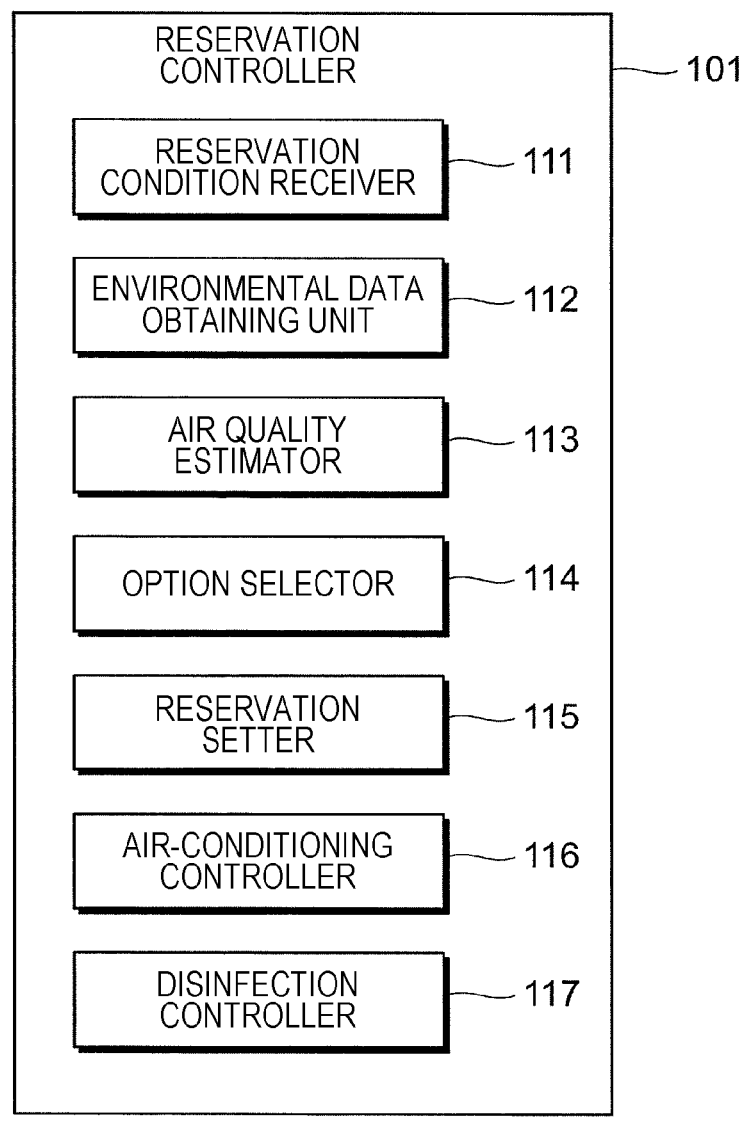
FIG. 6 is a block diagram illustrating an example of the software configuration of a central processing unit (CPU)

FIG. 6 is a block diagram illustrating an example of the software configuration of the CPU 51A.

The CPU 51A implements the corresponding functions by executing a program.

In this exemplary embodiment, the CPU 51A has the function of assisting a user in reserving a space 3 by estimating, based on a reservation status, the air quality within a space 3 (see FIG. 2) at a start time of a reservation for this space 3.

In this exemplary embodiment, this function is called a reservation controller 101. The reservation controller 101 is an example of an estimator.

In this exemplary embodiment, a reservation status means information concerning how reservations have been made for a certain space 3 on a time axis.

For example, a time difference between a certain reservation and the previous reservation is an example of the reservation status. When a new reservation is received, the reservation controller 101 judges whether to accept this reservation by considering, not only this reservation itself, but also a time difference between this reservation and a future reservation which follows this reservation. In this exemplary embodiment, for all reservations made to the spaces 3, the air quality satisfies a predetermined standard at the start time of a reservation.

A reservation is identified by information concerning the location which identifies a space 3 and a time period (start time and end time). Individual reservations are recorded in the reservation list 52 (see FIG. 1).

The reservation controller 101 includes multiple functions.

More specifically, the reservation controller 101 includes a reservation condition receiver 111, an environmental data obtaining unit 112, an air quality estimator 113, an option selector 114, a reservation setter 115, an air-conditioning controller 116, and a disinfection controller 117. The reservation condition receiver 111 receives conditions requested by a user. The environmental data obtaining unit 112 obtains environmental data concerning the air quality from each space 3. The air quality estimator 113 estimates the air quality at a start time of a reservation to be made for a space 3. The option selector 114 selects spaces 3 that satisfy conditions (conditions for a reservation) requested by a user as options. The reservation setter 115 sets a specific option selected by a user as a space 3 to be reserved. The air-conditioning controller 116 controls the operation of the air conditioner 31A (see FIG. 5) installed in each space 3. The disinfection controller 117 controls the operation of the disinfection unit 31V (see FIG. 5) installed in each space 3.

The reservation condition receiver 111 provides the function of receiving conditions for a reservation from a user using the user terminal 4 (see FIG. 1). Examples of the conditions for a reservation are a location and a time period. The time period is identified by a start time and an end time. Other examples of the conditions for a reservation may be facilities installed in a space 3 and a service provider.

The environmental data obtaining unit 112 communicates with a space 3 to obtain values from various sensors, such as the temperature sensor 31P, the humidity sensor 31Q, and the air environmental monitor 31U, installed in the space 3.

The air quality estimator 113 provides the function of estimating the air quality at a start time of a reservation to be made for a space 3 on the assumption that the conditions requested by a user are accepted.

Basically, the air quality estimator 113 estimates the air quality by using information concerning a blank time between the end of a certain reservation and the start of the following reservation.

If the performance of the air conditioner 31A (see FIG. 5) and that of the disinfection unit 31V (see FIG. 5) are known, given with the information concerning the above-described blank time, the air quality estimator 113 can fairly accurately estimate the air quality at a start time of a reservation to be made for a space 3 on the assumption that the space 3 will be used under the normal conditions.

In reality, however, the spaces 3 are used differently depending on the user. The type and the strength of odor which remains after the use of a space 3 also vary. For example, if a space 3 is used for eating and drinking, the smell of food is more likely to remain. The smell of perfume may remain in a space 3 depending on the type and the volume of perfume. The taste for odor is different depending on the individual user. Some users may like a certain odor, while other users may not like it. Not only the odor, the temperature or the humidity may also be changed depending on the use of a space 3.

In this exemplary embodiment, the air quality that varies depending on the use of a space 3 is determined by using the values measured by various sensors, and is used for estimating the air quality at a start time of the next reservation. If the air quality at the end of the use of a space 3 deviates from a predetermined standard, it takes a long time for the air quality to return to the predetermined standard.

If conditions for a reservation are received while a space 3 is being used, the air quality at the end of the use of a space 3 may be estimated from the values measured by the sensors at a time point when the conditions have been received.

The option selector 114 selects as options spaces 3 in which the estimated air qualities satisfy the predetermined standard and which satisfy the conditions requested by a user. The estimated air qualities of the spaces 3 may be presented on a screen of the user terminal 4 (see FIG. 1), or may be used only for internal processing executed by the reservation controller 101.

The reservation setter 115 sets a specific space 3 selected by a user from among the options as a space 3 to be reserved.

The air-conditioning controller 116 is used for remotely controlling the operation of the air conditioner 31A (may simply be a ventilation device) installed in each space 3.

The disinfection controller 117 is used for remotely controlling the operation of the disinfection unit 31V installed in each space 3. [Examples of Control Operation]

Examples of the reservation control operation implemented under the control of the reservation controller 101 (see FIG. 6) will be described below.
[First Example of Reservation Control Operation]

An example of the disposition of spaces 3 will first be discussed. The reservation controller 101 manages reservations for the spaces 3.

Figure 7:
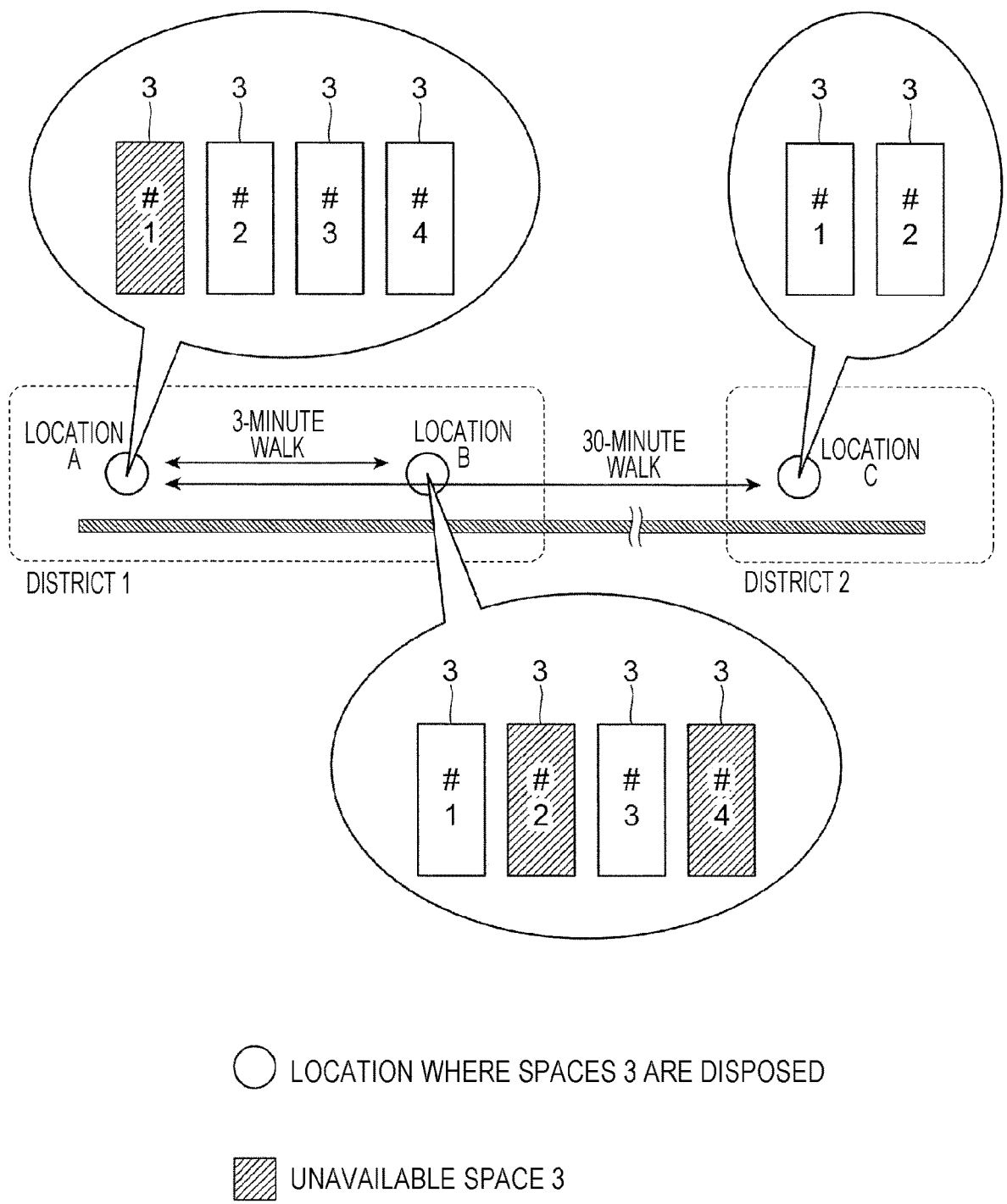
FIG. 7 illustrates an example of the disposition of spaces in a real space.

FIG. 7 illustrates an example of the disposition of spaces 3 in a real space.

FIG. 7 shows two areas managed as district 1 and district 2. The districts may be determined based on the administrative division or on another factor. The districts may alternatively be determined by using a building, such as a city hall or a department store, or a landmark as a start point.

In an individual district, one or plural locations are included. In the example in FIG. 7, location A and location B are included within district 1, while location C is included in district 2.

In each location, one or multiple spaces 3 are disposed. For example, four spaces 3 are disposed in location A, four spaces 3 are disposed in location B, and two spaces 3 are disposed in location C.

The individual spaces 3 are distinguished from each other by the name and the ID number indicated within the location.

Information concerning the districts, locations, and ID numbers is also used in the registration list 51 (see FIG. 1) and the reservation list 52 (see FIG. 1).

In FIG. 7, available spaces 3 and unavailable spaces 3 are displayed such that they can be distinguished from each other.

Figure 8:
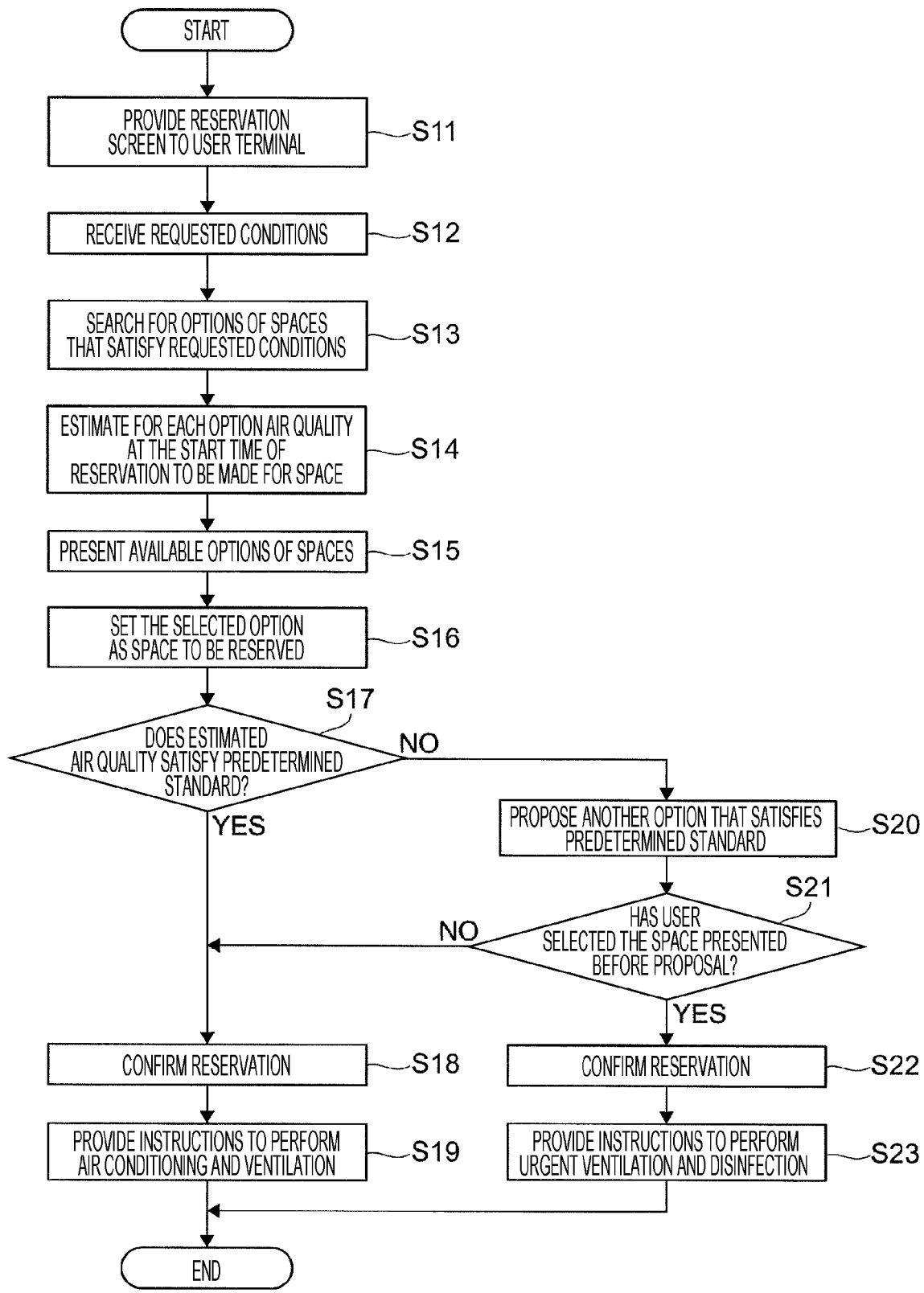
FIG. 8 is a flowchart illustrating an example of a control operation executed by a reservation controller.

FIG. 8 is a flowchart illustrating an example of a control operation executed by the reservation controller 101.

In step S11, the reservation controller 101 provides a screen for a reservation to the user terminal 4 (see FIG. 1).

Figure 9:
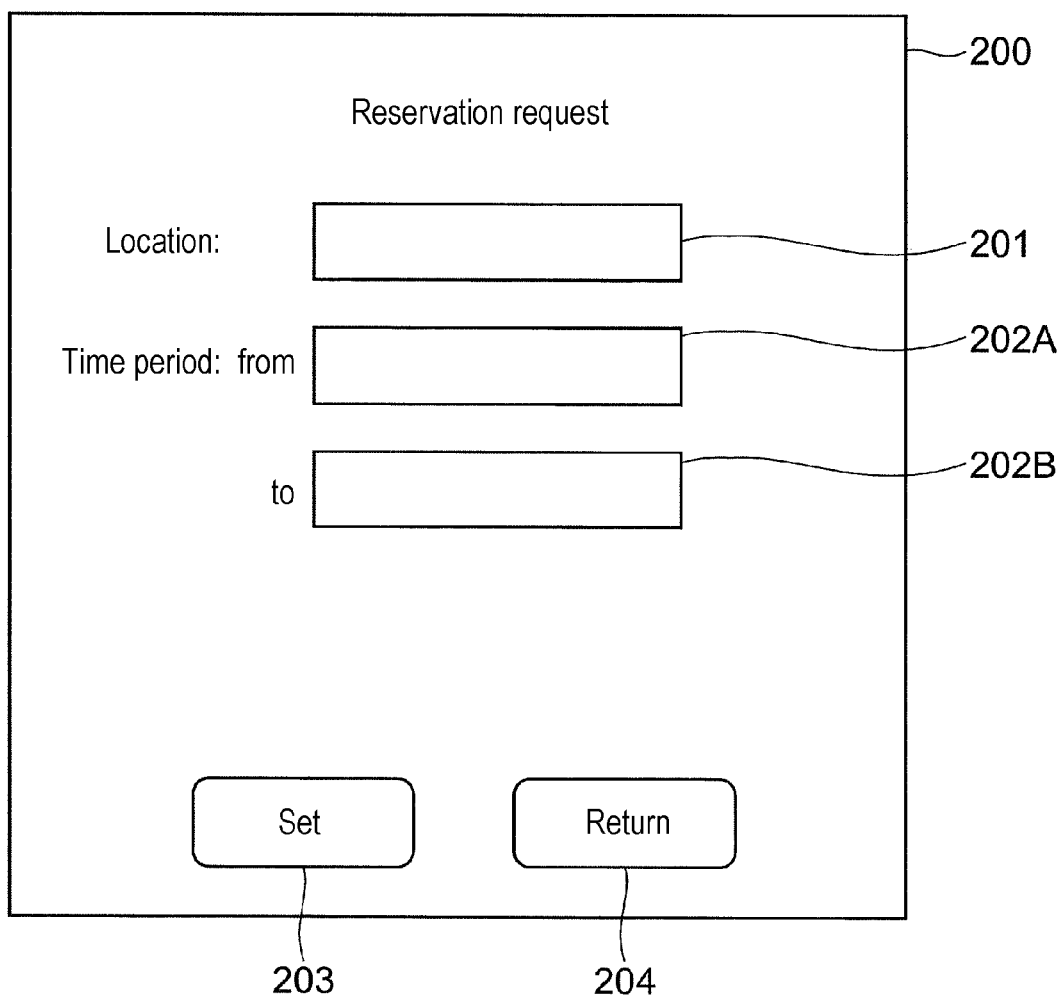
FIG. 9 illustrates a reservation-request receive screen displayed on a display device of the user terminal.

FIG. 9 illustrates a reservation-request receive screen 200 displayed on the display device 47 (see FIG. 3) of the user terminal 4.

The reservation-request receive screen 200 includes an input fields 201, 202A, and 202B. The input field 201 is used for inputting a location where a space 3 will be reserved. The input fields 202A and 202B are used for inputting a time period for which a space 3 will be reserved. More specifically, the input field 202A is used for inputting a start time, while the input field 202B is used for inputting an end time.

A user may directly input a location into the input field 201 and a time period into the input fields 202A and 202B, or may select options from provided items. The location may be input by the name of a place or the name of a district. Characters identifying a space 3 may be input as a location.

At the bottom of the reservation-request receive screen 200, a set button 203 for setting input information and a return button 204 for canceling input information are disposed.

Referring back to FIG. 8, in step S12, the reservation controller 101 receives the requested conditions input on the reservation-request receive screen 200 (see FIG. 9).

Then, in step S13, the reservation controller 101 searches for options of spaces 3 that satisfy the requested conditions. At this stage, options of spaces 3 that satisfy the location and the time period requested by the user are only extracted.

Then, in step S14, the reservation controller 101 estimates for each option the air quality at a start time of a reservation to be made for a space 3.

Figure 10:
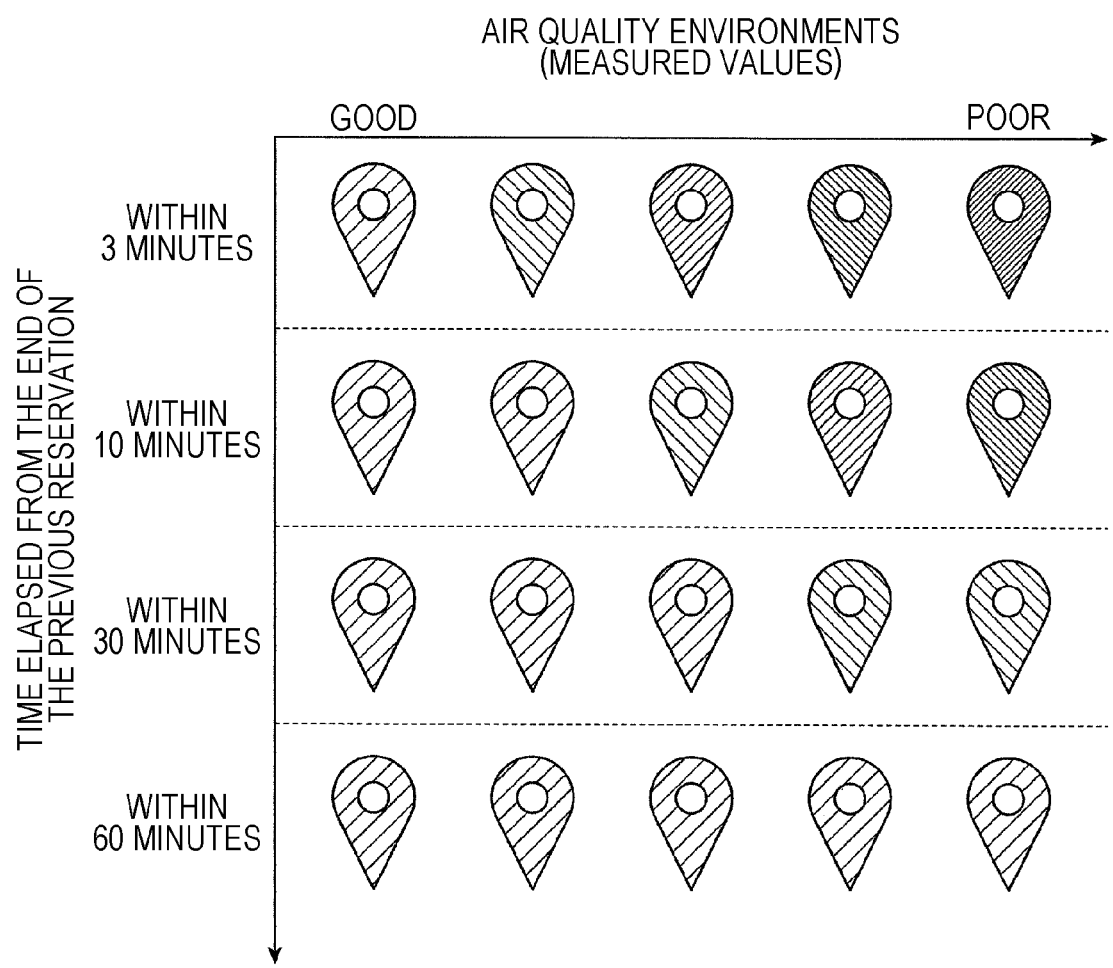
FIG. 10 illustrates examples of estimated air qualities.

FIG. 10 illustrates examples of the estimated air qualities.

The horizontal axis indicates the air quality in a space 3 at the end of the use of the space 3. As the space 3 is positioned toward the left side, the air quality is better. As the space 3 is positioned toward the right side, the air quality is poorer. The vertical axis indicates a time elapsed from the end of the use of a space 3. If the user has left a space 3 earlier than the end time of the reservation period, the earlier time is used as the end time of the reservation period.

In the example in FIG. 10, the air qualities have been estimated, on the assumption that the performance of the air conditioner 31A (may simply be a ventilation device) and that of the disinfection unit 31V are fixed. If the performance of the air conditioner 31A and that of the disinfection unit 31V are changeable, the time required for the spaces 3 to recover from a poor air quality may be longer or shorter than the times shown in FIG. 10.

FIG. 10 shows that, as the air quality in a space 3 at the end of the use of the space 3 is better, the next reservation can be started sooner.

In the example in FIG. 10, the air quality is indicated by the density of the hatched portion of a drop mark. As the density of the hatched portion is higher, the air quality is poorer.

Referring back to FIG. 8, in step S15, the reservation controller 101 presents the selected options on the user terminal 4 (see FIG. 1) operated by the user.

At this stage, the air qualities of spaces 3 are disregarded, and spaces 3 that are available in the requested time period are presented as options.

Figure 11:
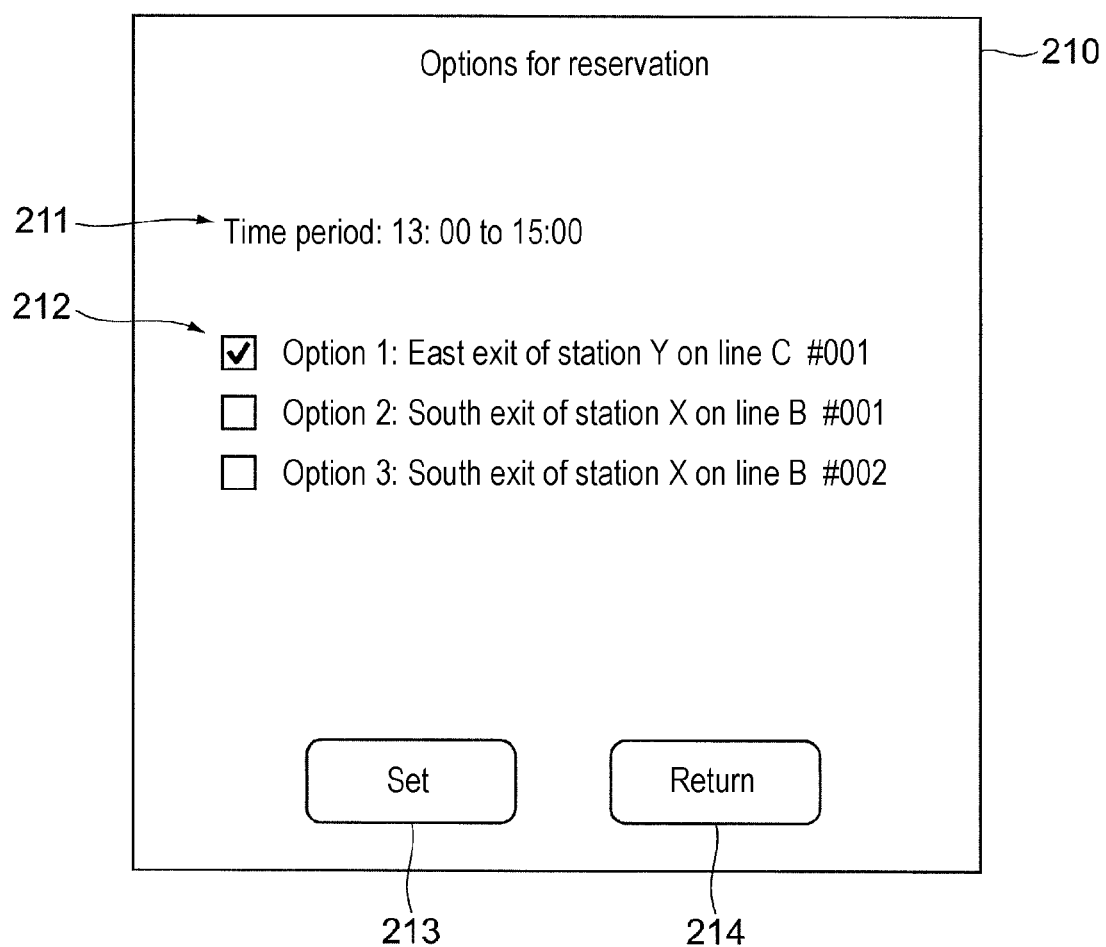
FIG. 11 illustrates an example of a screen on which options of available spaces are displayed in text.
Figure 12:
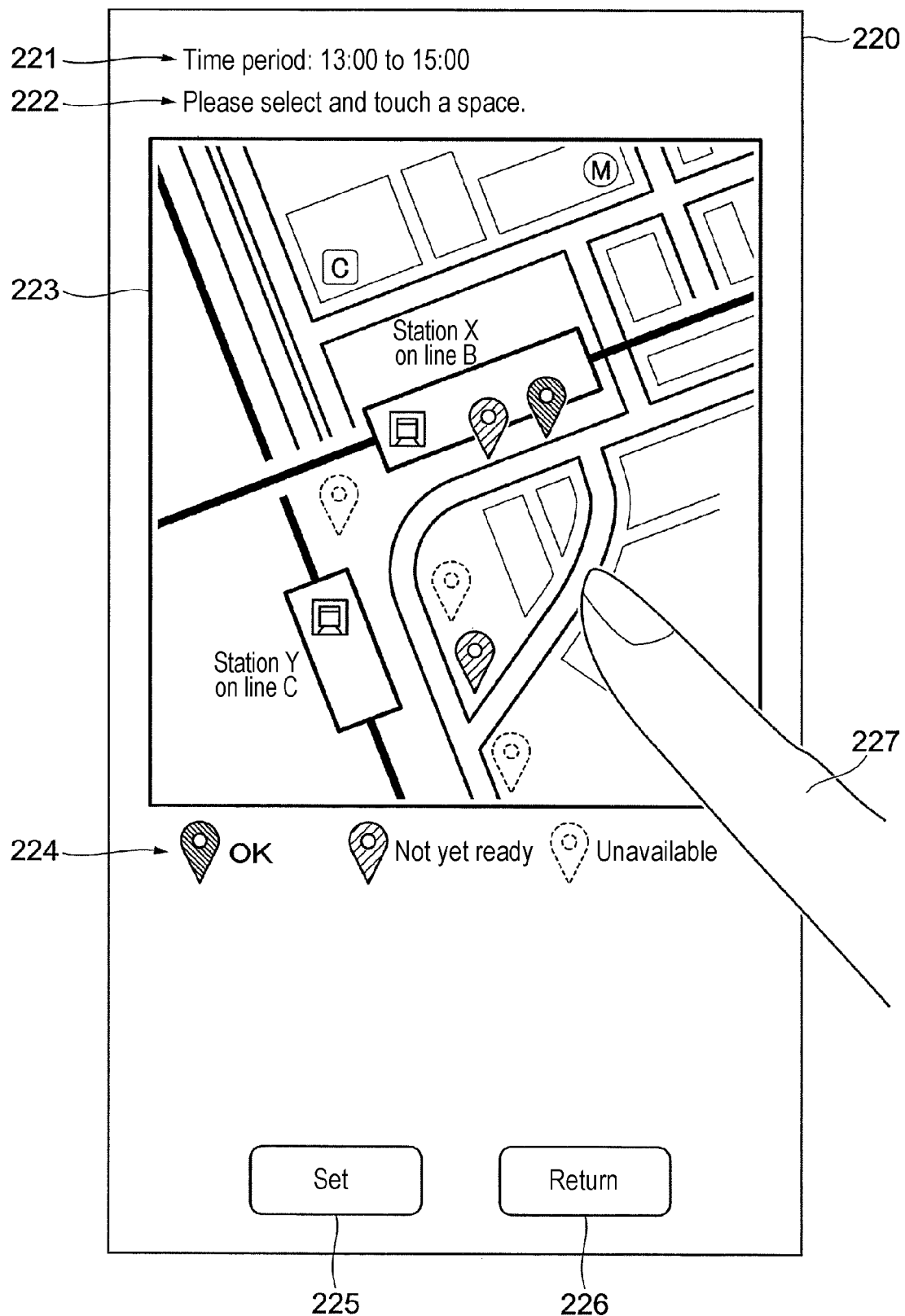
FIG. 12 illustrates an example of a screen on which the positions of available spaces are indicated on a map.

Examples of screens used for presenting options of available spaces 3 are shown in FIGS. 11 and 12.

FIG. 11 illustrates an example of the screen on which options of available spaces 3 are displayed in text.

FIG. 12 illustrates an example of the screen on which the positions of available spaces 3 are indicated on a map.

A reservation option screen 210 in FIG. 11 includes fields 211 and 212. In the field 211, the time period requested by a user is displayed. In the field 212, options of available spaces 3 are displayed. At the bottom of the reservation option screen 210, a set button 213 for setting a selected option, and a return button 214 for canceling a selected option are disposed.

In the field 211, the time period received on the reservation-request receive screen 200 (see FIG. 9) is displayed. In this example, the requested time period is 13:00 to 15:00.

In the field 212, three spaces 3 that satisfy the requested location and time period are displayed in text. Check boxes are added next to the spaces 3. When the user checks one of the check boxes and operates the set button 213, the selected option is set. When the user operates the return button 214, the reservation option screen 210 returns to the reservation-request receive screen 200.

A reservation option screen 220 in FIG. 12 includes fields 221 through 224. In the field 221, the time period requested by a user is displayed. In the field 222, the operation requested for the user to perform is displayed. In the field 223, the positions of options of available spaces 3 are indicated on a map. In the field 224, legends explaining the drop marks in the map are indicated. At the bottom of the reservation option screen 220, a set button 225 for setting a selected option, and a return button 226 for canceling a selected option are disposed.

When the user touches the drop mark of a desired space 3 with a finger 227 and operates the set button 225, the selected option is set. When the user operates the return button 226, the reservation option screen 220 returns to the reservation-request receive screen 200.

In the reservation option screen 220 in FIG. 12, the three options shown in FIG. 11 are displayed on the map. This enables the user to check the actual positions of the spaces 3 on the map.

In the field 224, the legend "OK" means that the air quality satisfies the predetermined standard, and the legend "not yet ready" means that the air quality will be lower than the predetermined standard at a start time of a reservation to be made for a space 3. Although in the example in FIG. 12 the availability of a space 3 (whether a space 3 is ready for a reservation) is indicated by a difference in the density of the drop mark, it may be expressed by a difference in the shape or the color of the drop mark. The rough time to be taken for a space 3 to get ready or the current air quality may also be indicated by a difference in the density, shape, or color of the drop mark, for example.

For example, the time required for the air quality to return to the predetermined standard, such as whether it takes about ten minutes or twenty minutes, may be indicated by a difference in the density, shape, or color of the drop mark. This enables the user to estimate the air quality. The drop mark for the space 3 may be changed according to the air quality.

Referring back to FIG. 8, in step S16, after the user has selected an option, the reservation controller 101 sets the selected option as a space 3 to be reserved.

The reservation controller 101 then judges in step S17 whether the estimated air quality in the space 3 to be reserved satisfies the predetermined standard.

If the estimated air quality satisfies the predetermined standard (YES in step S17), the reservation controller 101 confirms the reservation in step S18.

Figure 13:
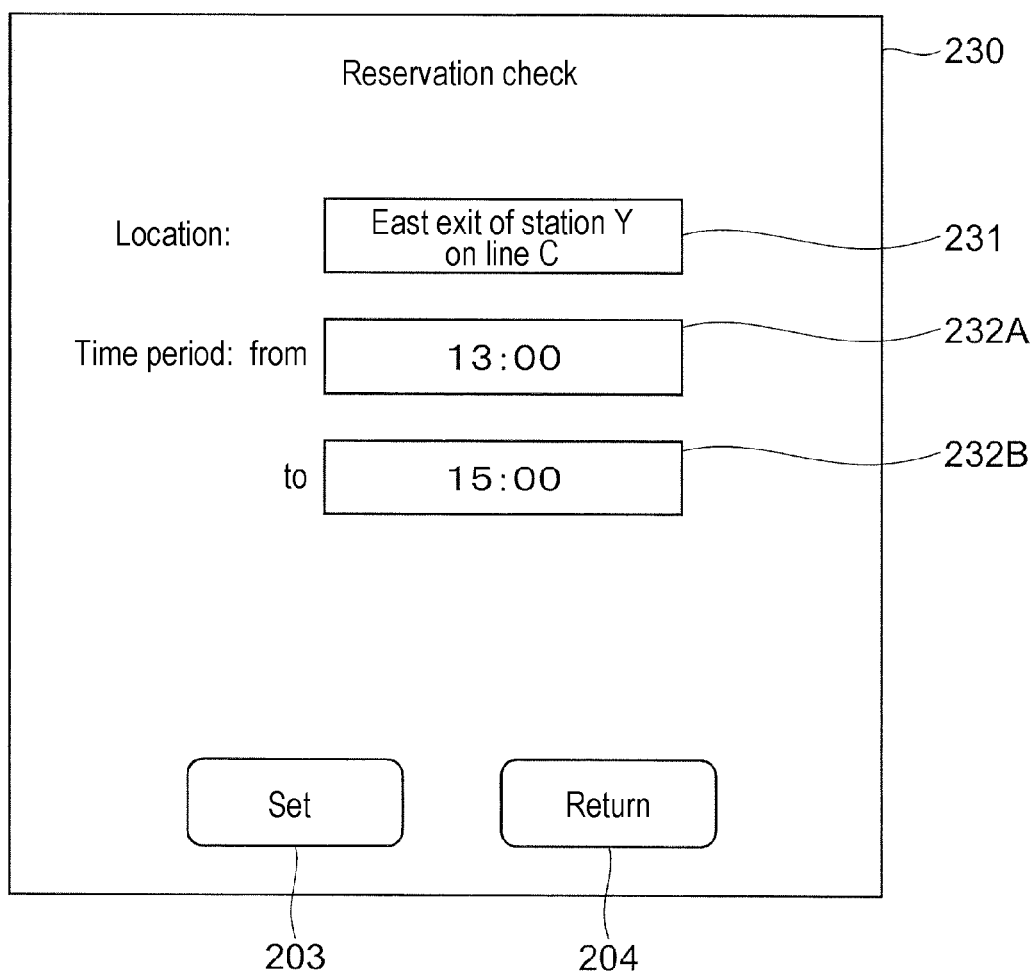
FIG. 13 illustrates an example of a screen when a reservation is confirmed.

FIG. 13 illustrates an example of the screen when the reservation is confirmed.

A reservation check screen 230 in FIG. 13 includes fields 231, 232A, and 232B. In the field 231, the location of the reserved space 3 is indicated. In the fields 232A and 232B, the time period is indicated. More specifically, the field 232A is used for indicating a start time, while the field 232B is used for indicating an end time.

Referring back to FIG. 8, after the reservation check screen 230 has been displayed, in step S19, the reservation controller 101 instructs the air conditioner 31A to perform air conditioning and a ventilation device (not shown) to conduct ventilation in the reserved space 3.

If air conditioning and ventilation have already started, the reservation controller 101 instructs the air conditioner 31A and the ventilation device to continue operation.

If it is found in step S17 that the estimated air quality does not satisfy the predetermined standard (NO in step S17), the reservation controller 101 proposes another option of a space 3 that satisfies the predetermined standard in step S20.

In this example of control operation, the user is able to select a space 3 that is not ready yet. When options are presented on the screen, such as that in FIG. 11 or 12, information concerning the air quality of each option may not necessarily be presented.

The reservation controller 101 proposes another space 3 having a better air quality. Several different approaches are possible for the reservation controller 101 to propose an alternative space 3. When proposing an alternative space 3, the difference in the charge for the spaces 3 and the installed facilities are disregarded.

In one approach, priority may be given to a space 3 disposed at the same location as that of a space 3 selected by a user. This can save the user the trouble of moving by a long distance. In the example in FIG. 11, #001 at East exit of station Y on line C is the space 3 requested by the user, and a space 3 managed by the location name "East exit of station Y on line C" is preferentially proposed.

If a space 3 managed by the same location name as that of the selected space 3 is not found, the reservation controller 101 proposes a space 3 that is managed by another location name in the neighborhood and also that satisfies the predetermined air quality standard. In the example in FIG. 11, among the spaces 3 managed by the location name "South exit of station X on line B, a space 3 that satisfies the predetermined air quality standard is proposed.

In another approach, to extend the search range of options, options may be selected according to the time taken to reach a space 3. In this case, the time for reaching a space 3 may be changed according to the location. For example, the time for reaching a space 3 in a downtown may be set to be longer, while the time for reaching in space 3 a residential area may be set to be shorter. Conversely, the time for reaching a space 3 in a downtown area may be set to be shorter, and the time for reaching a space 3 in a residential area may be set to be longer. The time to be set may be determined by a service provider in advance by considering the user convenience or by an individual user by itself.

In another approach, to extend the search range of options, options may be selected by the name of a location positioned near the location of the space 3 selected by the user. In this case, all locations near the subject location may be set as a search range, or they may be narrowed down to locations that satisfy a predetermined condition (locations near East exit, for example).

In another approach, to extend the search range of options, a specific location linked to the location of the space 3 selected by the user may be set as a search range.

In another approach, to extend the search range of options, the locations or spaces 3 on or near a route to a destination assumed from a schedule of the user may be set as a search range. Selecting of options based on the route to a user destination may be convenient for the user.

Figure 14:
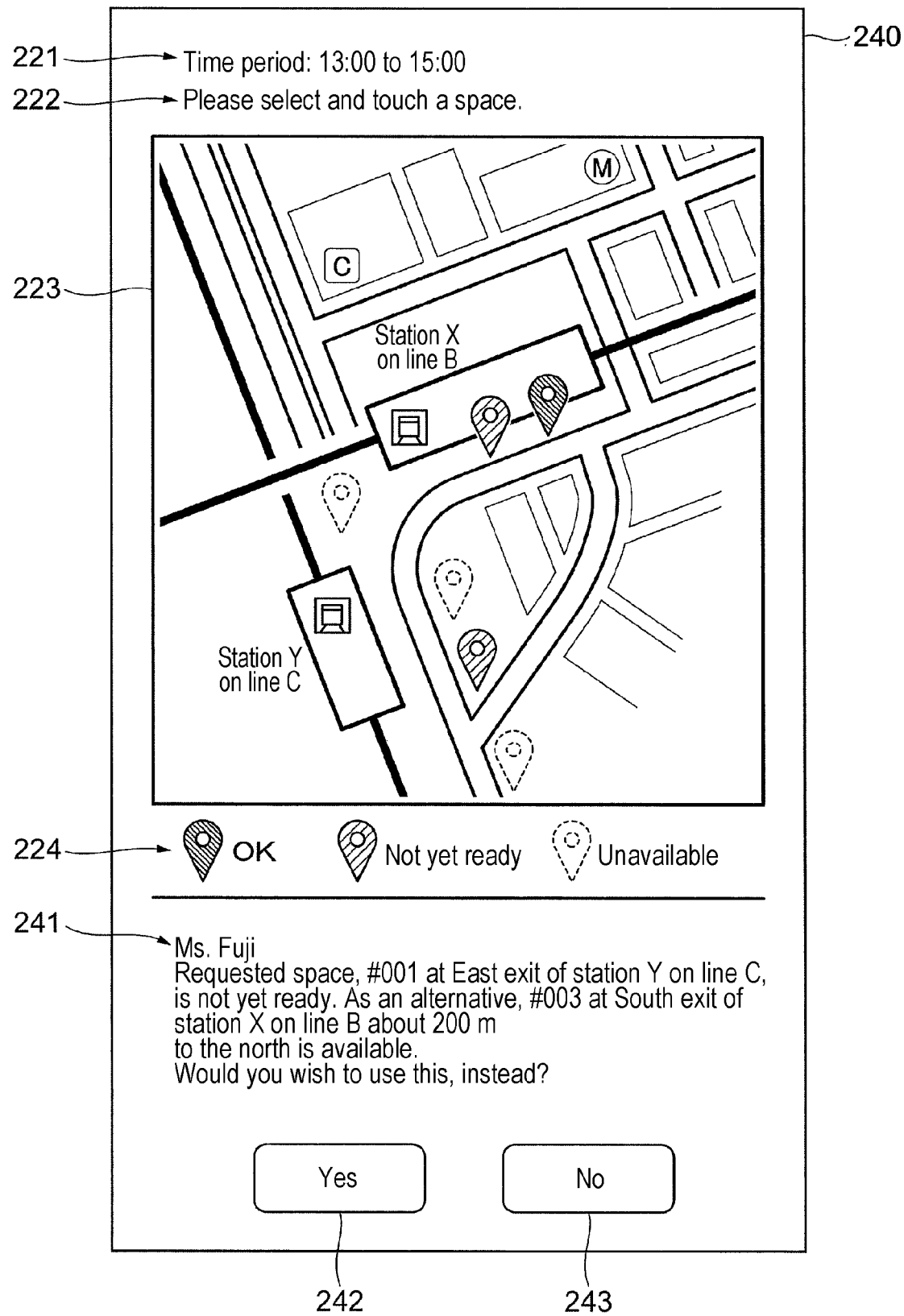
FIG. 14 illustrates an example of a screen for proposing an alternative option.

FIG. 14 illustrates an example of the screen for proposing an alternative option.

In FIG. 14, portions corresponding to those shown in FIG. 12 are designated by like reference numerals. An alternative-option proposal screen 240 is different from the reservation option screen 220 in that a field 241 and buttons 242 and 243 are disposed. In the field 241, a message for proposing another option is described. The button 242 is used for accepting the proposal, and the button 243 is used for rejecting the proposal.

In this example, a space 3 disposed in another location (South exit of station X on line B) different from the location (East exit of station Y on line C) of the space 3 requested by the user is proposed.

Referring back to FIG. 8, the reservation controller 101 judges in step S21 whether the user has still selected the space 3 set in step S16. The user may make a decision which one of the selected space 3 and the alternative space 3 will be used.

If the alternative space 3 is selected (NO in step S21), the reservation controller 101 proceeds to step S18 to confirm the reservation. The alternative space 3 proposed in step S20 satisfies the predetermined air quality standard at a start time of a reservation made for this space 3.

If the user has selected the space 3 that does not satisfy the predetermined air quality standard (YES in step S21), the reservation controller 101 proceeds to step S22 to confirm the reservation.

Then, in step S23, the reservation controller 101 provides instructions to perform urgent ventilation and disinfection for the reserved space 3.

In this exemplary embodiment, urgent ventilation is a mode in which the air volume per unit time processed by the air conditioner 31A or the ventilation device (not shown) is higher than that in the regular mode (step S19). When urgent ventilation is performed, the time required to improve the air quality is shorter than that in the regular mode, but sound of the air conditioner 31A and the ventilation device is louder.

Examples of a reservation process conducted under the above-described control operation will be discussed below with reference to FIGS. 15A through 15D.

FIGS. 15A and 15B illustrate a first example of a reservation process. FIG. 15A illustrates the state of a reservation at a time point in step 1 and FIG. 15B illustrates the state of the reservation at a time point in step 2.

FIG. 15C illustrates a second example of a reservation process. FIG. 15D illustrates a third example of a reservation process. FIG. 15C illustrates the state of a reservation at a time point in step 3 and FIG. 15D illustrates the state of a reservation at a time point in step 4.

The state of the reservation in step 1 in FIG. 15A will first be discussed. In step 1, the reservation statuses of four spaces 3 disposed at East exit of station Y on line C requested by user A are shown.

East exit of station Y on line C is a location name and #001 through #004 are numbers which identify the four spaces 3 disposed at East exit of station Y on line C.

It is assumed that user A wishes to reserve a space 3 from 15:30 to 17:00. In this example, the spaces 3 identified by #001, #002, and #003 are available.

The space 3 identified by #002 has the longest blank time after the previous reservation, the space 3 identified by #003 has the second longest blank time, and the space 3 identified by #001 has the shortest blank time.

If the spaces 3 are used under the normal conditions, the air quality at the start time (15:30) of the reservation is likely to be the best in the space 3 #002.

However, one hour and half can be secured as a blank time before user A starts to use the space 3 #003. The air quality at the start time of a reservation to be made for the space 3 #003 may be almost the same as that in the space 3 #002.

In terms of the blank time before the next reservation starts, thirty minutes can be secured before the next reservation in the space 3 #002, while there is no blank time before the next reservation in the spaces 3 #001 and #003.

If no blank time is secured before the next reservation starts, it is highly likely that the air quality at the start time of the next reservation will not satisfy the predetermined standard. Fifteen minutes are required as a blank time, provided that the spaces 3 are used under the normal conditions. The space 3 that the user can select is thus limited to the space 3 #002.

At the time point in step 2 in FIG. 15B, a reservation 250 is made in the space 3 #002 from 15:30 to 17:00.

In step 3 in FIG. 15C, user B wishes to reserve a space 3 at East exit of station Y on line C from 14:00 to 15:00.

In this example, the spaces 3 identified by #002, #003, and #004 are available.

The space 3 #002 has the longest blank time after the previous reservation, while the spaces 3 #003 and #004 have almost no blank time.

In terms of the blank time before the next reservation, the space 3 #003 has the longest blank time, the space 3 #004 has the second longest blank time, and the space 3 #002 has the shortest blank time. However, thirty minutes can be secured as a blank time for the space 3 #002 and are long enough to get ready for the next reservation.

In this example, the highest priority is given to the space 3 #002 that satisfies the air quality standard at the start of a reservation to be made for the space 3 by user B and also at the start of the next reservation. The space 3 #003 has the second highest priority, and the space 3 #004 has the lowest priority.

At the time point in step 3 in FIG. 15C, a reservation 251 is made in the space 3 #002 from 14:00 to 15:00.

If user B wishes to reserve the space 3 #003 or #004, a reservation may be made (YES in step S21 of FIG. 8).

In step 4 in FIG. 15D, user C wishes to reserve a space 3 at East exit of station Y on line C from 15:00 to 17:00.

In this example, the space 3 identified by #003 is available. However, no blank time is secured in the space 3 #003 before the next reservation.

Then, in step 4, South exit of station X on line B located near East exit of station Y on line C is added to the search range.

Four spaces 3 managed by the location name of South exit of station X on line B are all available.

However, after the previous reservations, no blank time is secured in the spaces 3 identified by #001 and #004, and thus, the spaces 3 #001 and #004 have a lower priority.

Fifteen minutes or longer are secured in the spaces 3 #002 and #003 after the previous reservations and also before the next reservations. The spaces 3 #002 and #003 thus have a higher priority. In this example, a reservation 252 is made in the space 3 #003 having a longer blank time after the previous reservation. [Second Example of Reservation Control Operation]

Another example of the reservation control operation implemented under the control of the reservation controller 101 (see FIG. 6) will be described below with reference to FIG. 16.

Figure 16:
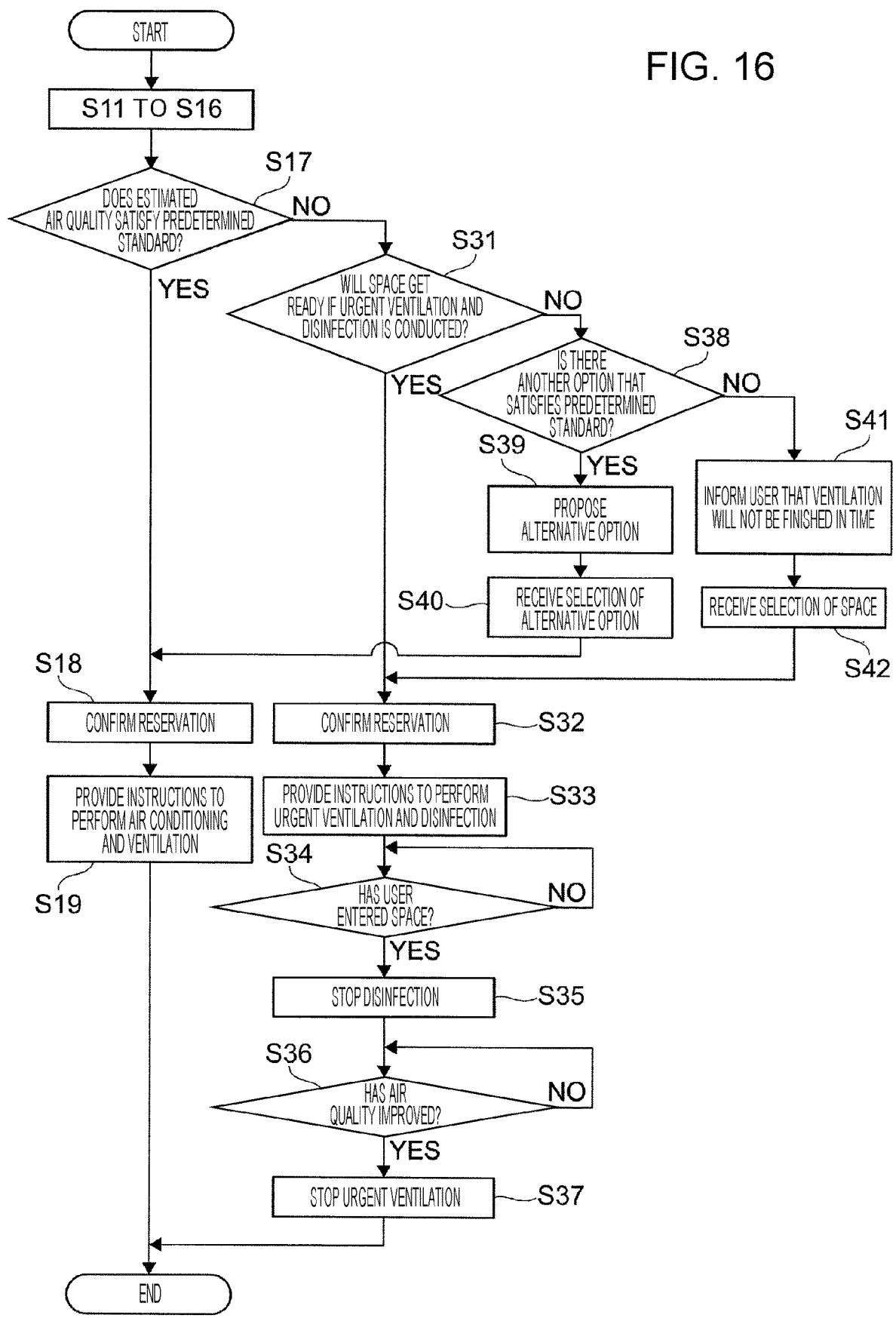
FIG. 16 is a flowchart illustrating another example of a control operation executed by the reservation controller.

In FIG. 16, steps corresponding to those shown in FIG. 8 are designated by like step numbers. Steps S11 through S19 are the same as those in FIG. 8.

A case in which the result of step S17 is NO will be discussed.

If it is found in step S17 that the estimated air quality does not satisfy the predetermined standard, the reservation controller 101 judges in step S31 whether the space 3 will become ready if urgent ventilation and disinfection are performed. "Becoming ready" refers to that the air quality in the space 3 satisfies the predetermined standard before the use of the space 3 (start time of a reservation for this space 3).

If the result of step S31 is YES, the reservation controller 101 confirms the reservation in step S32, and provides instructions to conduct urgent ventilation and disinfection in step S33.

Then, the reservation controller 101 starts monitoring and judges whether a user has entered the space 3 in step S34. While the result in step S34 is NO, step S34 is repeated. If the result of step S34 is YES, the reservation controller 101 provides an instruction in step S35 to stop disinfection to protect the user from UV rays. Urgent ventilation continues.

Then, the reservation controller 101 judges in step S36 whether the air quality has improved. While the result of step S36 is NO, step S36 is repeated. If the result of step S36 is YES, the reservation controller 101 stops urgent ventilation in step S37.

If the air quality does not satisfy the predetermined standard even if urgent ventilation is conducted, the result of step S31 becomes NO.

In this case, the reservation controller 101 determines in step S38 whether another option is available to satisfy the predetermined air quality standard.

If the result of step S38 is YES, the reservation controller 101 proposes an alternative option. The alternative option satisfies the predetermined air quality standard, and the user accepts it in step S40. Then, the reservation controller 101 proceeds to step S18.

If it is found in step S38 that no option is available to satisfy the predetermined standard, in step S41, the reservation controller 101 informs the user that the selected space 3 will not be ready in time. For example, the reservation controller 101 informs the user that ventilation in the space 3 will not be over in time and the ventilation sound may be loud. If the user accepts this situation and still wishes to reserve the space 3, the reservation controller 101 receives this selection in step S42. The reservation controller 101 then proceeds to step S32.

Figure 17:
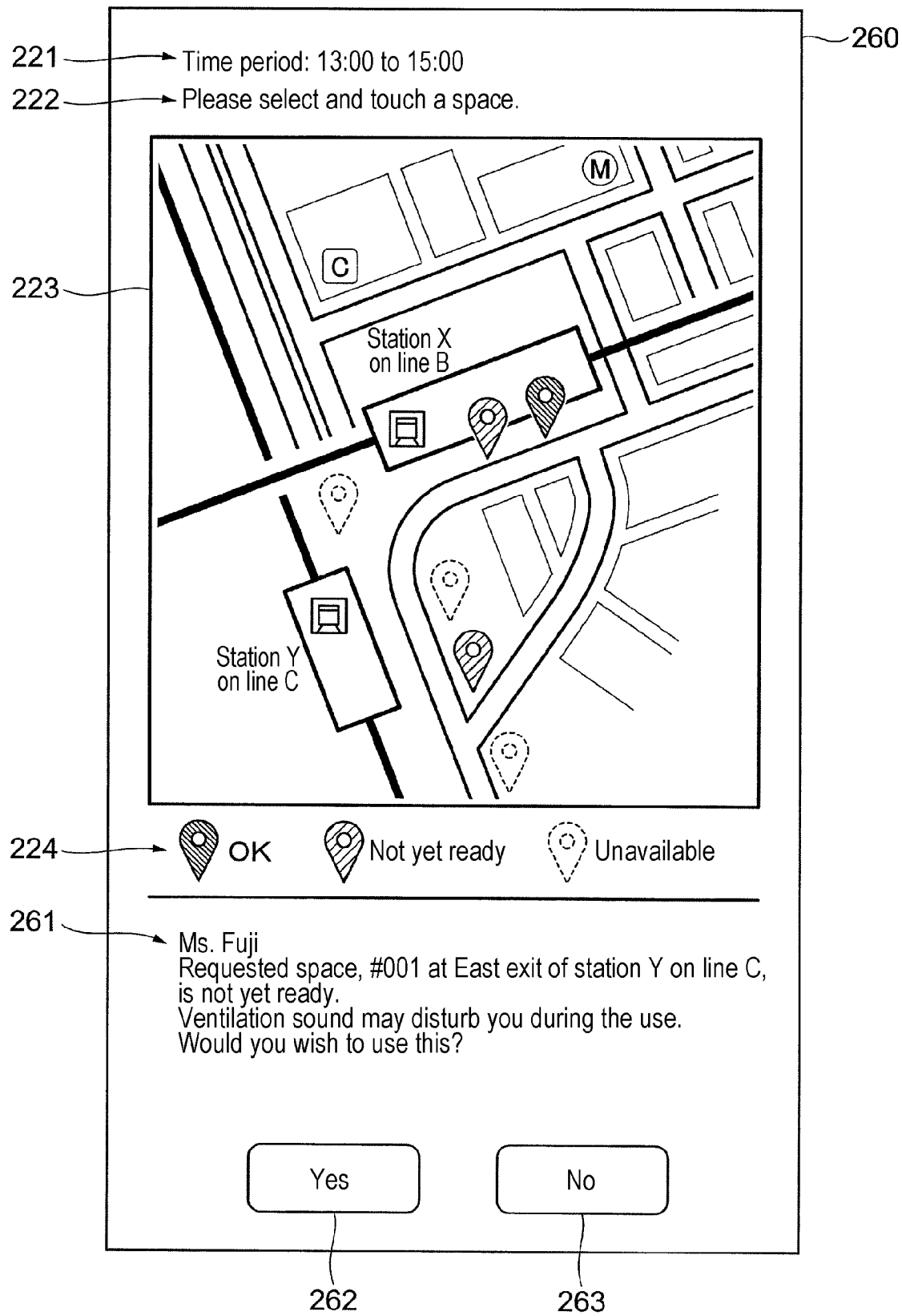
FIG. 17 illustrates an example of a screen for receiving a reservation for a space that needs urgent ventilation.

FIG. 17 illustrates an example of the screen for receiving a reservation for a space 3 that needs urgent ventilation.

In FIG. 17, portions corresponding to those shown in FIG. 14 are designated by like reference numerals.

In a field 261, a message that the space 3 requested by a user is not ready yet and ventilation sound may be loud during the use of the space 3 is described.

If the user accepts this situation, it operates a button 262. Then, the reservation controller 101 proceeds to step S32. If the user does not accept this situation, it operates a button 263. In this case, a proposal to extend the search area to find an alternative option, for example, is presented.
[Example of Control Operation after Use of Space]

A control operation executed after a user has left a space 3 will be discussed below.

Figure 18:
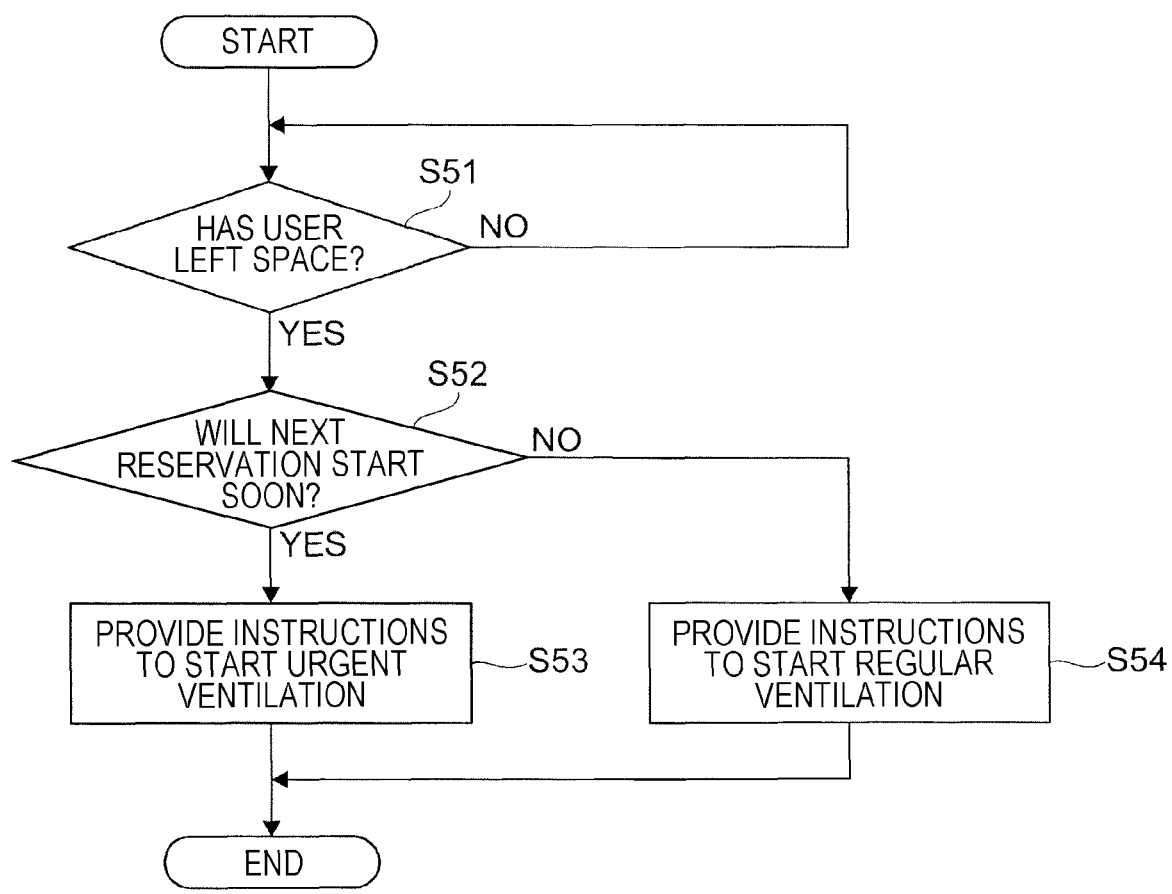
FIG. 18 is a flowchart illustrating an example of a control operation executed by the reservation controller after a user has left a space.

FIG. 18 is a flowchart illustrating an example of a control operation executed by the reservation controller 101 after a user has left a space 3.

In step S51, the reservation controller 101 judges whether a user has left a space 3. While the result of step S51 is NO, step S51 is repeated.

If it is found in S51 that the user has left the space 3 (YES in step S51), the reservation controller 101 judges in step S52 whether the next reservation for the space 3 will start soon. This judgement is made also by considering the air quality based on values measured by sensors.

If the result of step S52 is YES, the reservation controller 101 provides instructions to start urgent ventilation in step S53. More specifically, the reservation controller 101 provides instructions to open the ventilation vent unit 31W and to disinfect the space 3 with a deodorizing spray. If the result of step S52 is NO, the reservation controller 101 provides instructions to start regular ventilation in step S54. More specifically, the reservation controller 101 provides instructions to open the ventilation vent unit 31W and to disinfect the space 3 with a deodorizing spray.

Figure 19:
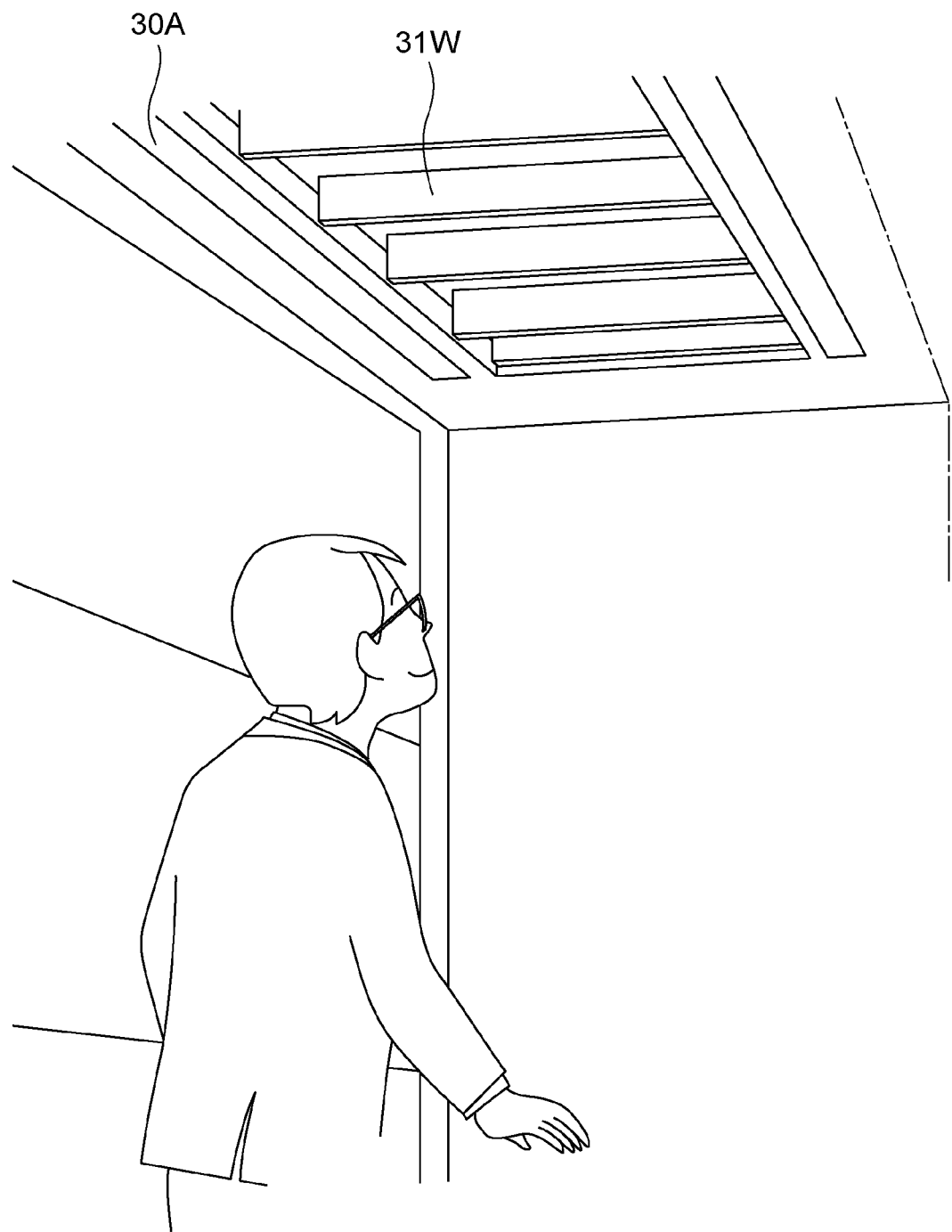
FIG. 19 illustrates a ventilation vent unit which is fully opened.

FIG. 19 illustrates the ventilation vent unit 31W which is fully opened. In this exemplary embodiment, the ventilation vent unit 31W, which is part of the ventilation device, forms part of the ceiling 30A.

FIG. 20 illustrates examples of the states of equipment installed in a space 3 at individual time points when the space 3 is in preparation, ready, and being used.

In FIG. 20, the ON/OFF state of outdoor LEDs installed on the outside walls (walls 30D and 30E) of a space 3, the illumination state of indoor lighting, the ON/OFF state of the UV LED, the operation state of the air conditioner, and the open/close state of the ventilation vent unit are shown in association with the individual time points.

In the example in FIG. 20, the outdoor LEDs are turned ON when a space 3 is not used and are turned OFF when a space 3 is used.

The indoor lighting is turned ON when a space 3 is used and is turned OFF or glimmers when a space 3 is not used.

The UV LED is turned ON for disinfection only when a space 3 is in preparation.

The air conditioner 31A is operated in the urgent mode or in the regular mode when a space 3 is in preparation.

The ventilation vent unit 31W is fully opened when a space 3 is in preparation.

According to this exemplary embodiment, it is possible to decide whether a reservation for a space 3 will be accepted by considering the air quality at the reservation start time for the space 3.

A space 3 that satisfies a predetermined air quality standard and also that is close enough to a place requested by the user is preferentially presented as an option. For example, a space 3 disposed in the same location as that of a space 3 requested by a user is presented. This saves the user the trouble of moving by a long distance.

Other Exemplary Embodiments

The exemplary embodiment of the invention has been discussed above. However, the technical scope of the invention is not restricted to the exemplary embodiment. Various modifications and/or improvements may be made, and exemplary embodiments based on such modifications and improvements are also encompassed within the technical scope of the invention.

For example, in the above-described exemplary embodiment, a user reserves a space 3 by using the user terminal 4 (see FIG. 1). However, the user may use a user interface installed in a space 3.

Figure 21:
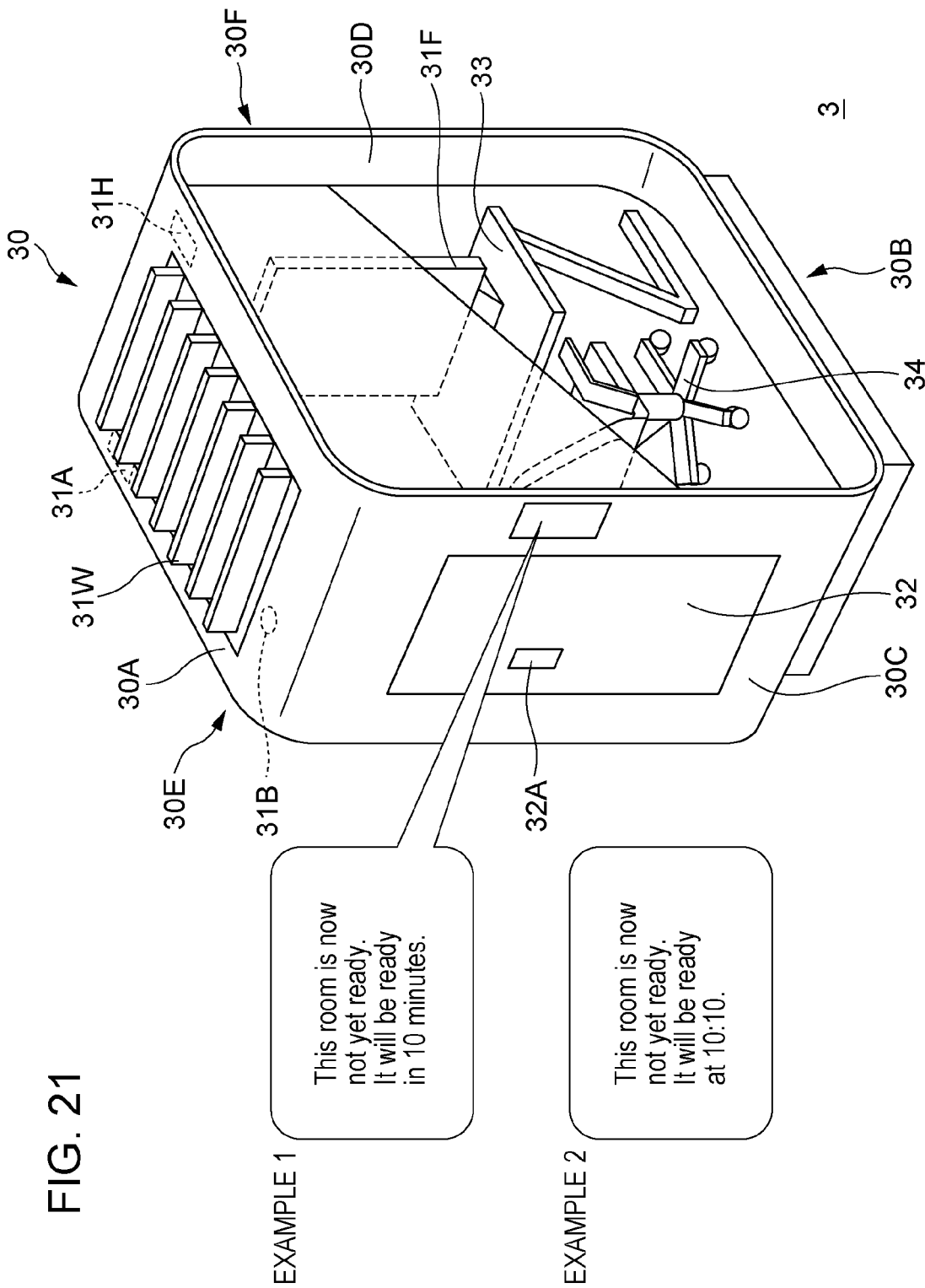
FIG. 21 illustrates another example of a space.

FIG. 21 illustrates another example of a space 3. In this space 3, the display device 31M is provided on an outside wall. In FIG. 21, a function of informing a user of an estimated time required for the space 3 to become ready (that is, the estimated time for the space 3 to satisfy the air quality standard) is shown. In Example 1, the waiting time is indicated. In Example 2, the specific time is indicated.

In the above-described exemplary embodiment, when a user has input conditions for a reservation, a screen for presenting the states of spaces 3 at the start time of the reservation is displayed. Alternatively, the air qualities of spaces 3, for example, at the time when a user has input conditions may be provided to the user.

Figure 22:
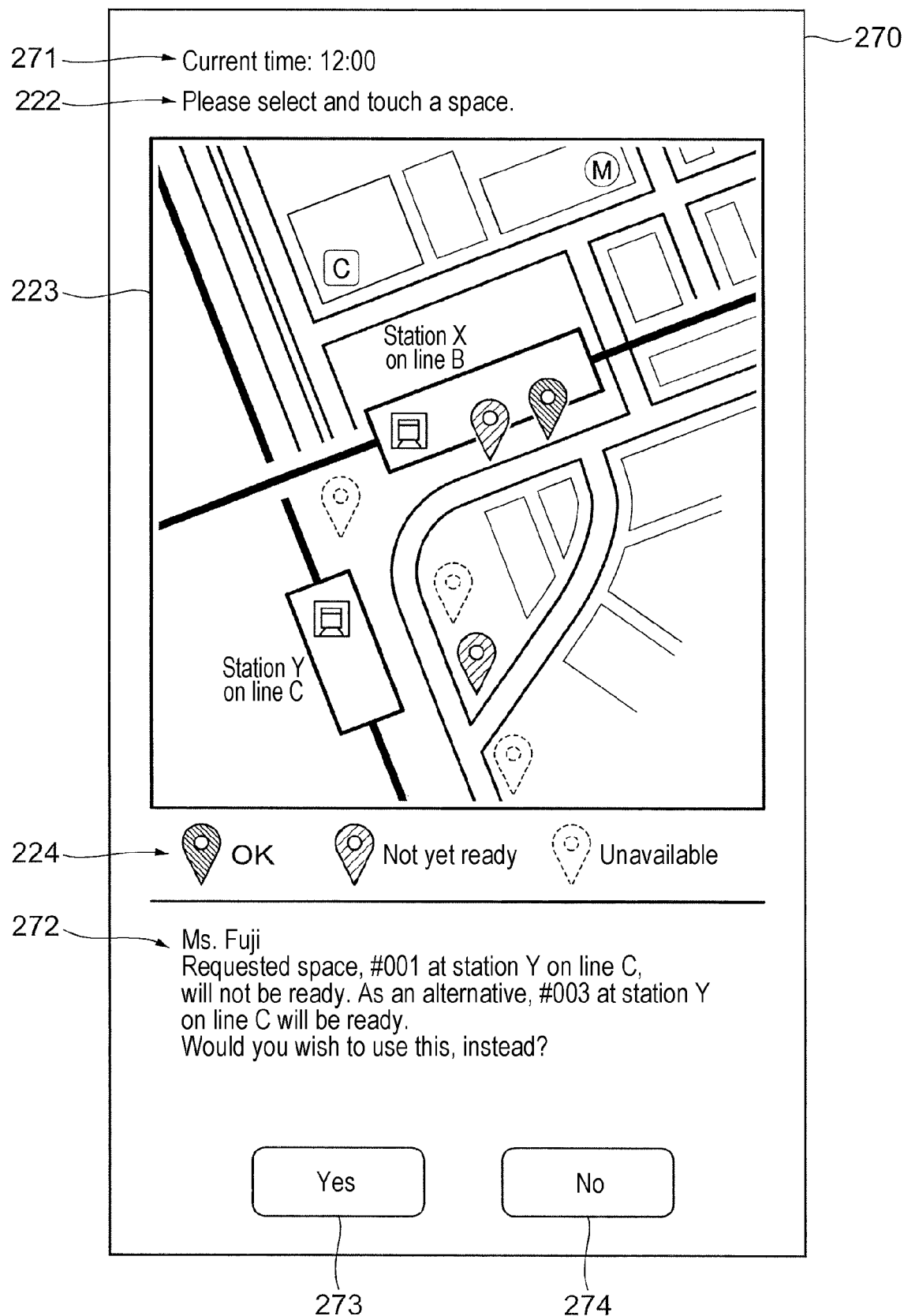
FIG. 22 illustrates an example of a screen for presenting the air qualities of spaces at the time when a user has input conditions for a reservation and for receiving a reservation request from the user.

FIG. 22 illustrates an example of the screen for presenting the air qualities of spaces 3 at the time when a user has input conditions for a reservation and for receiving a reservation request from the user.

In FIG. 22, portions corresponding to those shown in FIG. 17 are designated by like reference numerals.

On a reservation-request receive screen 270, a field 271 for indicating a current time is provided.

In a field 223, a map of a location requested by the user is displayed, and spaces 3 in this location are disposed on the map.

In the example in FIG. 22, the states of the spaces 3 in the field 223 are those at the current time. The user can estimate how long it will take for each space 3 displayed in the field 223 to become ready, though it is unknown to the user whether the spaces 3 can be reserved.

In a field 272, an example of a message after the user has selected a time period and a specific space 3 to be reserved is displayed. In this example, the space 3 is not yet ready in the requested time period (space 3 does not satisfy the air quality standard) and an alternative option is proposed.

In the above-described exemplary embodiment, the air quality in an individual space 3 is estimated and presented to a user. However, the representative value of the air qualities in multiple spaces 3 in each location may be presented, instead. In this case, the representative value may be given as a typical value of the air qualities estimated for multiple spaces 3 in the same location based on the majority vote rule.

In the above-described exemplary embodiment, a user selects a specific space 3 from among available spaces 3 (step S16 in FIG. 8). A user may alternatively select a location. In this case, if no spaces 3 disposed at the selected location satisfy the predetermined air quality standard, options of spaces 3 may be searched for in another location linked to the selected location or in another location that satisfies a predetermined condition.

In the above-described exemplary embodiment, not only available spaces 3, but also unavailable spaces 3 and those that are not yet ready, are displayed on the screen (see FIG. 12). However, only available spaces 3 or spaces 3 that satisfy a predetermined condition may be presented to a user as options. Examples of the predetermined condition are that a space 3 will be ready if urgent ventilation is performed and that a space 3 will be ready in five minutes.

Figure 23:
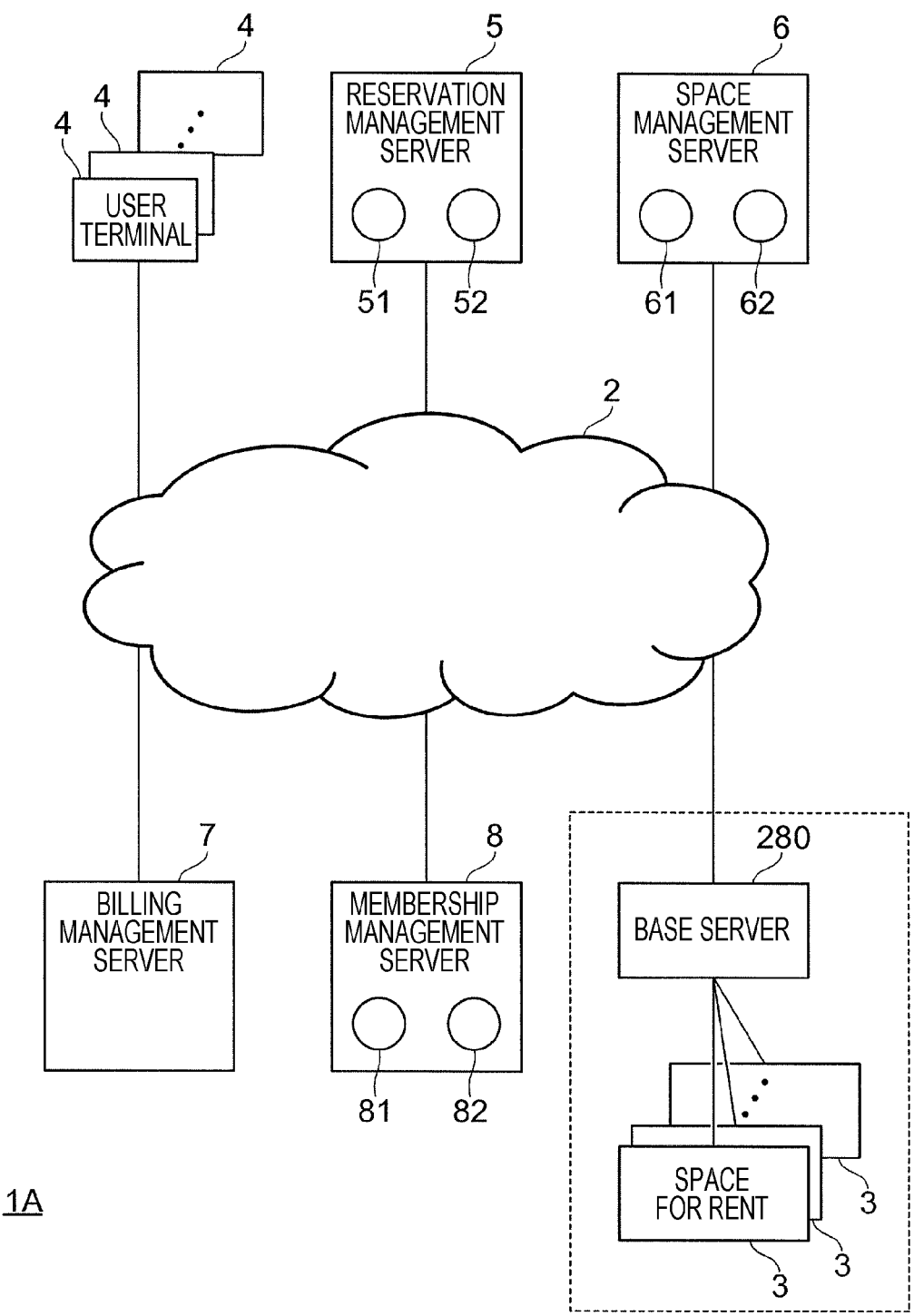
FIG. 23 schematically illustrates another example of the configuration of the management system.

The management system 1 (see FIG. 1) is not restricted to the above-described configuration. FIG. 23 schematically illustrates another example of the configuration of the management system 1, that is, the configuration of a management system 1A. In FIG. 23, elements corresponding to those in FIG. 1 are designated by like reference numerals. The management system 1A is different from the management system 1 in that a base server 280 is used for managing the plural spaces 3. The base server 280 configured as a computer may perform the functions of the reservation controller 101 (see FIG. 6) by executing a program. In this sense, the base server 280 is an example of the apparatus.

In the above-described exemplary embodiment, a small room having a soundproof function, such as that shown in FIG. 2, is assumed as a space 3. However, meeting rooms, study rooms, and various types of guest rooms may be used as spaces 3 if reservations are required to be made for renting the spaces 3.

The above-described exemplary embodiment has been described, assuming that the door 32 can be locked. However, the above-described control function is still applicable when the door 32 is not possible to lock.

In the above-described exemplary embodiment, the spaces 3 are rented on a time basis. However, the spaces 3 may be rented based on another factor.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A room comprising:
    a skeleton that forms a space which is closed for an exterior;
    an air conditioner and disinfection unit that improves an air quality within the space;
    an informing device including a display disposed at an exterior of the room, to inform users at the exterior of the space by displaying a request for reserving the room received by a reservation controller and information indicating a time estimated by the reservation controller for the air quality to reach a predetermined standard based on amount of blank time prior to the start time during which the room is free of any reservation and capability of air conditioner installed in the space,
    wherein the request for reserving the room includes a start time of reservation of the room, and
    the time required for the air quality to satisfy the predetermined standard from the start time is estimated by the reservation controller.

2. The room according to claim 1, wherein the time is provided according to the air quality within the space which is estimated based on a reservation status.

3. An apparatus comprising:
    a memory, storing a program; and
    a reservation controller including a processor, executing the program to be configured to:
    receive a plurality of conditions requested by a user, wherein the conditions include a start time for a reservation of a space in a future time;
    obtain environmental data concerning an air quality within the space which is measured through an air environmental sensor;
    estimate the air quality within the space at the start time of the reservation to be made for the space based on amount of blank time prior to the start time during which the space is free of any reservation and capability of air conditioner installed in the space;
    display the space with the estimated air quality at the requested start time of the reservation for selection;
    set a special option selected by the user as the space to be reserved; and
    transmit a control signal to control an operation of an air conditioner installed in the space in response to a confirmation on the reservation of the space, and to control a ventilation device to ventilate the space and a disinfection unit to disinfect the air within the space so that the air quality at the start time of reservation reaches a predetermined standard.

4. The apparatus according to claim 3, wherein the space is closed for an exterior.

5. The apparatus according to claim 3, wherein, in a case in which one or a plurality of spaces are disposed in an individual location, if the air quality estimated for a specific space selected by a user does not satisfy the predetermined standard, another space that is disposed in a location in which the specific space is disposed is selected as an option.

6. The apparatus according to claim 5, wherein, if the option is not found in the location in which the specific space is disposed, another space that satisfies a condition determined for the specific space is selected as an option.

7. The apparatus according to claim 6, wherein the condition is provided as a time to be taken to reach a space.

8. The apparatus according to claim 7, wherein the time is changeable according to the location.

9. The apparatus according to claim 5, wherein, if the option is not found in the location in which the specific space is disposed, another space is selected as an option, based on a route of the user which is assumed from a schedule of the user.

10. The apparatus according to claim 3, wherein, in a case in which one or a plurality of spaces are disposed in an individual location, when a specific location is selected by a user, a space disposed in the specific location is selected as an option.

11. The apparatus according to claim 10, wherein, if the air quality estimated for each space disposed in the specific location does not satisfy the predetermined standard, a space disposed in another location linked to the specific location is selected as an option.

12. The apparatus according to claim 10, wherein, if the air quality estimated for each space disposed in the specific location does not satisfy the predetermined standard, a space in another location that satisfies a condition determined for the specific location is selected as an option.

13. The apparatus according to claim 12, wherein the condition is provided as a time to be taken to reach a location.

14. The apparatus according to claim 13, wherein the time is changeable according to the location.

15. The apparatus according to claim 3, wherein the estimated air quality is displayed as a representative of air qualities of a plurality of spaces disposed in an individual location.

16. The apparatus according to claim 3, wherein the estimated air quality is displayed according to the space.

17. The apparatus according to claim 15, wherein a symbol which represents a location or a space on a map displayed on a screen is indicated in a different mode according to the air quality.

18. The apparatus according to claim 17, wherein an unavailable space or a location in which all spaces are unavailable is displayed in a different mode from an available space or a location including an available space.

19. The apparatus according to claim 3, wherein, when a space which does not satisfy the predetermined standard of the air quality is selected by a user, the user is informed that ventilation sound is likely to occur.

20. The apparatus according to claim 3, wherein, when a space which does not satisfy the predetermined standard of the air quality is selected by a user, an instruction to increase a ventilation level is provided.

21. The apparatus according to claim 3, wherein the air quality is estimated based on a time difference with another reservation.

22. The apparatus according to claim 3, wherein the air quality is estimated according to the performance of ventilation.

23. The apparatus according to claim 3, wherein the air quality is estimated according to the performance of air conditioning.

24. The apparatus according to claim 3, wherein the air quality is estimated by using a value measured by a sensor.

25. The apparatus according to claim 3, wherein, not only the air quality at a start time of a certain reservation for a selected option, but also the air quality at a start time of the next reservation for the selected option are estimated.

26. A management system comprising:
a memory, storing management data concerning spaces for implementing a plurality of management functions; and
a reservation controller including a processor, executing the plurality of management functions to be configured to:
receive a plurality of conditions requested by a user, wherein the conditions include a start time for a reservation of a space in a future time;
obtain environmental data concerning an air quality within space which is measured through an air environmental sensor;
estimate the air quality within the space at the start time of the reservation to be made for the space based on amount of blank time prior to the start time during which the space is free of any reservation and capability of air conditioner installed in the space;
display the space with the estimated air quality at the requested start time of the reservation for selection;
set a special option selected by the user as the space to be reserved; and
transmit a control signal to control an operation of an air conditioner installed in the space in response to a confirmation on the reservation of the space, and to control a ventilation device to ventilate the space and a disinfection unit to disinfect the air within the space so that the air quality at the start time of reservation reaches a predetermined standard.

27. A non-transitory computer readable medium storing a program to be loaded by a processor of a reservation controller to execute a process, the process comprising:
receiving a plurality of conditions requested by a user, wherein the conditions include a start time for a reservation of a space in a future time;
obtaining environmental data concerning an air quality within a space which is measured through an air environmental sensor;
estimating the air quality within the space at the start time of the reservation to be made for the space based on amount of blank time prior to the start time during which the space is free of any reservation and capability of air conditioner installed in the space;
displaying the space with the estimated air quality at the requested start time of the reservation for selection;
set a special option selected by the user as the space to be reserved; and
transmitting a control signal to control an operation of an air conditioner installed in the space in response to a confirmation on the reservation of the space, and to control a ventilation device to ventilate the space and a disinfection unit to disinfect the air within the space so that the air quality at the start time of reservation reaches a predetermined standard.

* * * * *